United States Patent [19]
Zhang

[11] Patent Number: 5,885,936
[45] Date of Patent: Mar. 23, 1999

[54] HETEROTRICYCLIC HERBICIDES

[75] Inventor: Wei Zhang, Wilmington, Del.

[73] Assignee: E. I. du Pont de Nemours and Company, Wilmington, Del.

[21] Appl. No.: 19,143

[22] Filed: Feb. 6, 1998

Related U.S. Application Data

[60] Provisional application No. 60/039,147, Feb. 24, 1997.
[51] Int. Cl.$^6$ .......................... A01N 43/32; C07D 339/08
[52] U.S. Cl. ................................. 504/288; 549/16; 549/17
[58] Field of Search ..................... 549/16, 17; 504/288, 504/289

[56] References Cited

U.S. PATENT DOCUMENTS

| | | |
|---|---|---|
| 4,790,870 | 12/1988 | Hunt et al. . |
| 5,468,878 | 11/1995 | Nasuno et al. . |
| 5,480,858 | 1/1996 | Sakamoto et al. . |

FOREIGN PATENT DOCUMENTS

| | | |
|---|---|---|
| 0 219 451 A1 | 4/1987 | European Pat. Off. . |
| 0 283 261 A2 | 9/1988 | European Pat. Off. . |
| 0 606 843 A1 | 7/1994 | European Pat. Off. . |
| 0 629 623 A1 | 12/1994 | European Pat. Off. . |
| 0 712 853 A1 | 5/1996 | European Pat. Off. . |
| 0 728 756 A1 | 8/1996 | European Pat. Off. . |
| WO 94/04524 | 3/1994 | WIPO . |
| WO 94/08988 | 4/1994 | WIPO . |
| WO 95/04054 | 2/1995 | WIPO . |
| WO 95/13275 | 5/1995 | WIPO . |

*Primary Examiner*—Robert W. Ramuyer

[57] ABSTRACT

Compounds of Formula I, and their N-oxides and agriculturally suitable salts, are disclosed which are useful for controlling undesired vegetation

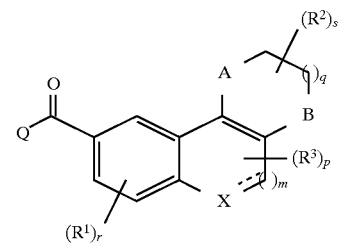

wherein Q, X, A, B, $R^1$ through $R^3$, m, p, q, r, and s are as defined in the disclosure.

Also disclosed are compositions containing the compounds of Formula I and a method for controlling undesired vegetation which involves contacting the vegetation or its environment with an effective amount of a compound of Formula I.

6 Claims, No Drawings

HETEROTRICYCLIC HERBICIDES

This application claims the priority benefit of U.S. Provisional Application 60/039,147, filed Feb. 24, 1997.

BACKGROUND OF THE INVENTION

This invention relates to certain heterotricyclic compounds, their N-oxides, agriculturally suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

WO 94/04524 discloses herbicidal cyclohexanedione derivatives of Formula i as herbicides:

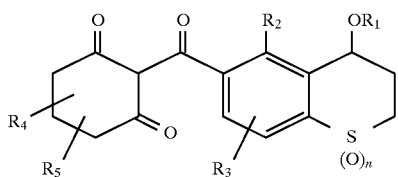

wherein, inter alia, $R_1$ is $C_1$–$C_6$ alkyl;

$R_2$ is $C_1$–$C_4$ alkyl;

$R_3$–$R_5$ are H or $C_1$–$C_4$ alkyl; and n is 0, 1 or 2.

The heterotricyclic compounds of the present invention are not disclosed in this publication.

SUMMARY OF THE INVENTION

This invention is directed to compounds of Formula I including all geometric and stereoisomers, N-oxides, and agriculturally suitable salts thereof, agricultural compositions containing them and their use for controlling undesirable vegetation:

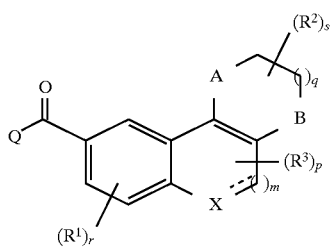

wherein
Q is

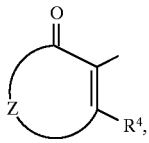

Q-1

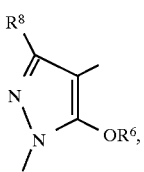

Q-2

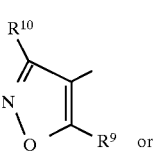

Q-3

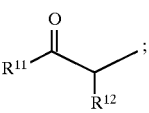

Q-4

Z is selected from the group —$CH_2CH_2CH_2$—, —$OCH_2CH_2$—, —O—CH=CH—, —$NR^{13}CH_2CH_2$—, —$NR^{13}CH=CH$—, —$N=CHCH_2$—, —$OCH_2O$—, —$NR^{13}CH_2NR^{13}$—, —$N=CHNR^{13}$—, —$CH_2OCH_2$—, —$CH_2NR^{13}CH_2$—, —$CH_2S(O)_nCH_2$—, —$CH_2C(O)CH_2$—, —CH=$NCH_2$—, —$CH_2CH_2$—, —$OCH_2$—, —$SCH_2$—, and —$NR^{13}CH_2$—, each group optionally substituted with one to four $R^5$, and the directionality of the Z linkage is defined such that the moiety depicted on the left side of the linkage is bonded to the carbonyl carbon of Q-1;

X is O, $S(O)_n$, $N(C_1-C_2$ alkyl), N, CH or $CH_2$ optionally substituted with 1–2 $C_1-C_2$ alkyl;

A is O or $S(O)_n$;

B is $S(O)_n$;

each $R^1$ is independently $C_1-C_6$ alkyl, $C_1-C_6$ haloalkyl, $C_1-C_6$ alkoxy, $C_1-C_6$ haloalkoxy, $S(O)_nR^{17}$, $SO_2N(R^{13})_2$, halogen, cyano or nitro;

each $R^2$ is independently $C_1-C_3$ alkyl;

each $R^3$ is independently $C_1-C_2$ alkyl;

$R^4$ is $OR^{14}$, SH, $S(O)_nR^{17}$, halogen or $NR^{15}R^{16}$; or $R^4$ is phenylthio or phenylsulfonyl, each optionally substituted with $C_1-C_3$ alkyl, halogen, cyano or nitro;

each $R^5$ is independently H, $C_1-C_3$ alkyl, $C_3-C_6$ alkenyl, $C_3-C_6$ alkynyl, $C_1-C_3$ alkoxy, formyl, $C_2-C_6$ alkoxycarbonyl, —$CH_2(C_1-C_3$ alkoxy), —$CH(C_1-C_3$ alkoxy)$_2$, $C_1-C_3$ alkylthio, cyano or halogen; or when two $R^5$ are attached to the same carbon atom, then said $R^5$ pair can be taken together to form —$OCH_2CH_2O$—, —$OCH_2CH_2CH_2O$—, —$SCH_2CH_2S$—or —$SCH_2CH_2S$—, each group optionally substituted with 1–4 $CH_3$;

$R^6$ is H, $C_1-C_6$ alkyl, $C_1-C_6$ haloalkyl, $C_2-C_6$ alkoxyalkyl, formyl, $C_2-C_6$ alkylcarbonyl, $C_2-C_6$ alkoxycarbonyl, $C_2-C_6$ alkylaminocarbonyl, $C_3-C_7$ dialkylaminocarbonyl or $SO_2R^{17}$; or $R^6$ is phenyl, benzyl, benzoyl, —$CH_2C(O)$phenyl or phenylsulfonyl, each optionally substituted on the phenyl ring with $C_1-C_3$ alkyl, halogen, cyano, or nitro;

$R^7$ is H, $C_1-C_6$ alkyl, $C_1-C_6$ haloalkyl, $C_3-C_6$ alkenyl, $C_3-C_6$ alkynyl or —$CH_2CH_2OR^{13}$; or $R^7$ is phenyl or benzyl, each optionally substituted on the phenyl ring with $C_1-C_3$ alkyl, halogen, cyano or nitro;

$R^8$ is H, $C_1-C_6$ alkyl, $C_1-C_6$ haloalkyl, halogen, cyano or nitro;

$R^9$ is H, $C_1-C_6$ alkyl, $C_1-C_6$ haloalkyl, $C_3-C_6$ cycloalkyl or $C_3-C_6$ halocycloalkyl;

$R^{10}$ is H, $C_2-C_6$ alkoxycarbonyl, $C_2-C_6$ haloalkoxycarbonyl, $CO_2H$ or cyano;

$R^{11}$ is $C_1-C_6$ alkyl, $C_1-C_6$ haloalkyl, $C_3-C_6$ halocycloalkyl or $C_3-C_6$ cycloalkyl optionally substituted with 1–4 $C_1-C_3$ alkyl;

$R^{12}$ is cyano, $C_2-C_6$ alkoxycarbonyl, $C_2-C_6$ alkylcarbonyl, $S(O)_nR^{16}$ or $C(O)NR^{15}R^{16}$; each $R^{13}$ is independently H or $C_1-C_6$ alkyl;

$R^{14}$ is H, $C_1-C_6$ alkyl, $C_1-C_6$ haloalkyl, $C_2-C_6$ alkoxyalkyl, formyl, $C_2-C_6$ alkylcarbonyl, $C_2-C_6$ alkoxycarbonyl, $C(O)NR^{15}R^{16}$ or $SO_2R^{17}$; or $R^{14}$ is phenyl, benzyl, benzoyl, —$CH_2C(O)$phenyl or phenylsulfonyl, each optionally substituted on the phenyl ring with $C_1-C_3$ alkyl, halogen, cyano or nitro;

$R^{15}$ is H or $C_1-C_6$ alkyl;

$R^{16}$ is $C_1-C_6$ alkyl or $C_1-C_6$ alkoxy; or $R^{15}$ and $R^{16}$ can be taken together as —$CH_2CH_2$—, —$CH_2CH_2CH_2$—, —$CH_2CH_2CH_2CH_2$—, —$CH_2$ or —$CH_2CH_2OCH_2CH_2$—;

$R^{17}$ is $C_1-C_6$ alkyl or $C_1-C_6$ haloalkyl;

m is 0, 1 or 2;

each n is independently 0, 1 or 2;

p is 0, 1 or 2;

q is 1 or 2;

r is 0, 1,2 or 3; and s is 0, 1,2,3 or 4;

provided that when m is 0 then X is other than N or CH; and wherein the dashed line in Formula I signifies either a single or double bond.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S$(O), $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The term "halogen", either alone or in compound words such as "haloalkyl", includes fluorine, chlorine, bromine or iodine. The term "1–2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. Examples of "haloalkoxy" include $CF_3O$, $CCl_3CH_2O$, $HCF_2CH_2CH_2O$ and $CF_3CH_2O$.

The total number of carbon atoms in a substituent group is indicated by the "$C_i$-$C_j$" prefix where i and j are numbers from 1 to 7. For example, $C_1-C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

When a group contains a substituent which can be hydrogen, for example $R^6$ or $R^7$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

Some compounds of this invention can exist as one or more tautomers. One skilled in the art will recognize, for example, that compounds of Formula Ia (Formula I where Q is Q-1, $R^4$ is $OR^{14}$, and $R^{14}$ is H) can also exist as the tautomers of Formulae Ib and Ic as shown below. One skilled in the art will recognize that said tautomers often exist in equilibrium with each other. As these tautomers interconvert under environmental and physiological conditions, they provide the same useful biological effects. The present invention includes mixtures of such tautomers as well as the individual tautomers of compounds of Formula I.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

Preferred compounds for reasons of better activity and/or ease of synthesis are:

Preferred 1. Compounds of Formula I above, and N-oxides and agriculturally suitable salts thereof, wherein:
Q is Q-1 or Q-2.

Preferred 2. Compounds of Preferred 1 wherein:
X is $SO_2$ or CH;
A and B are independently $S(O)_n$; and
$R^1$ is $C_1$–$C_3$ alkyl, halogen, cyano or nitro.

Preferred 3. Compounds of Preferred 2 wherein:
Q is Q-1;
Z is —$CH_2CH_2CH_2$—; and
$R^4$ is $OR^{14}$.

Preferred 4. Compounds of Preferred 2 wherein:
Q is Q-2; and
$R^7$ is $CH_2CH_3$.

Most preferred is the compound of Preferred 3 selected from the group:

2-[(2,3-dihydro-7,10-dimethyl-6,6-dioxido-5H- 1,4-dithiino [2,3-c][1]benzothiopyran-9-yl)carbonyl]-3-hydroxy-2-cyclohexen-1-one; and 2-[(2,3-dihydro-7,10-dimethylnaphtho[1,2-b]-1,4-dithiin-9-yl)carbonyl]-3-hydroxy-2-cyclohexen-1-one.

This invention also relates to herbicidal compositions comprising herbicidally effective amounts of the compounds of the invention and at least one of a surfactant, a solid

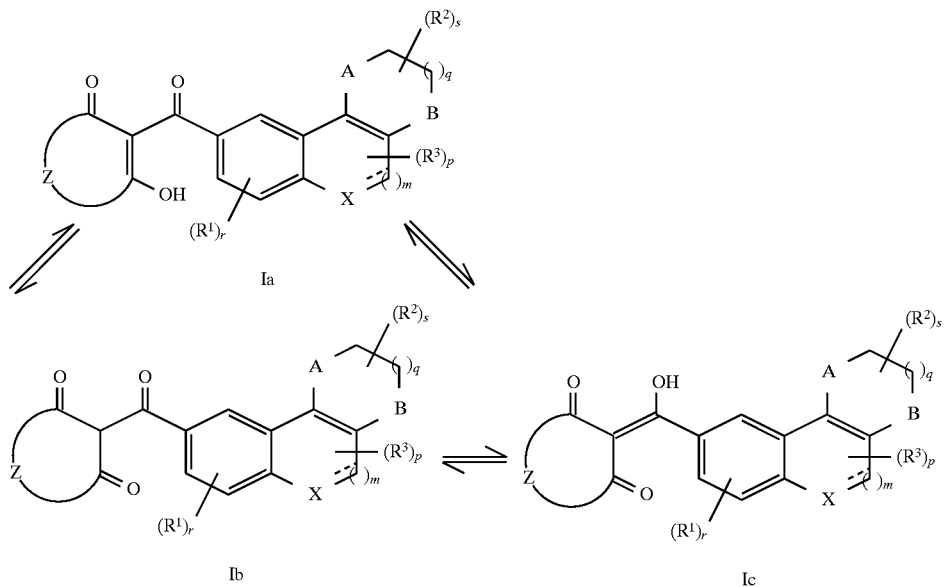

diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of the invention (e.g., as a composition described herein).

with a base such as triethylamine in the presence of a catalytic amount of a cyanide source (e.g., acetone cyanohydrin or potassium cyanide). This rearrangement is carried out by general methods known in the art; see for example, W. J. Michaely, EP 369,803-A1; D. Cartwright, et al., EP 283,261-B1.

Scheme 1

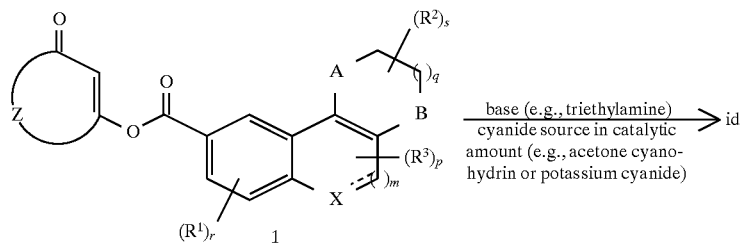

The preferred methods of use are those involving the above preferred compounds.

DETAILS OF THE INVENTION

The compounds of Formula I can be prepared by one or more of the following methods and variations as described in Schemes 1–17. The definitions of Q, $R^1$–$R^{17}$, Z, X, A, B, m, n, p, q, r, and s in the compounds of Formulae 1–17 below are as defined above in the Summary of the Invention. Compounds of Formulae Ia–Ig are subsets of the compounds of Formula I, and all substituents for Formulae Ia–Ig are as defined above for Formula I. For example, compounds of Formula Id below are compounds of Formula I wherein Q is Q-1.

Enol esters of Formula 1 can be prepared by reacting an acid chloride of Formula 2 with a dicarbonyl compound of Formula 3 in the presence of a slight molar excess of a base such as triethylamine in an inert organic solvent such as acetonitrile, dichloromethane or toluene at temperatures between 0° C. and 110° C. (Scheme 2). This type of coupling is carried out by methods known in the art (or by slight modification of these methods): for example, see W. J. Michaely, EP 369,803-A1 and D. Cartwright, et al., EP 283,261-B1.

Scheme 2

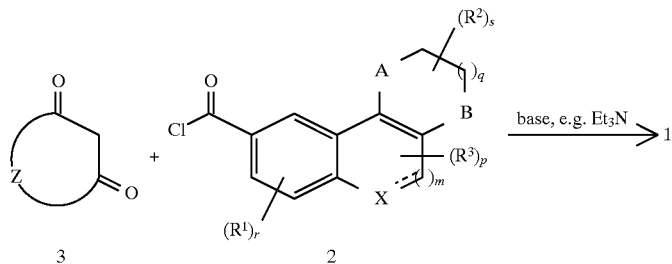

The acid chlorides of Formula 2 can be prepared by one skilled in the art by reacting acids of Formula 4 with chlorinating agents such as oxalyl chloride or thionyl chloride and a catalytic amount of dimethylformamide (Scheme 3). This chlorination is well known in the art: for example, see W. J. Michaely, EP 369,803-A1.

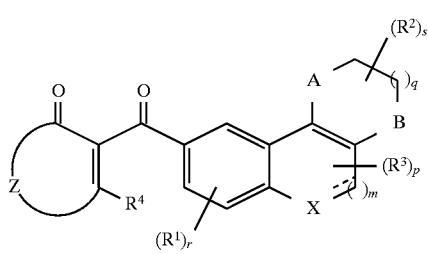

Scheme 3

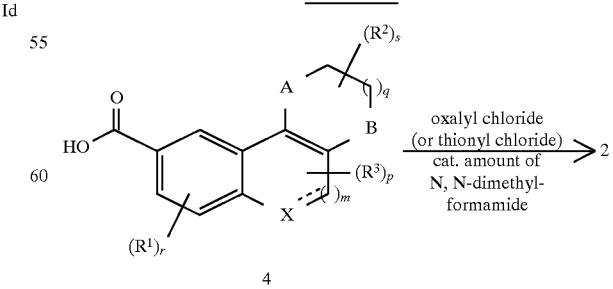

Scheme 1 illustrates the preparation of compounds of Formula Id whereby an enol ester of Formula 1 is reacted Enol esters of Formula 1 can be prepared by reacting the acid of Formula 4 with N-methyl-2-chloropyridinium iodide, followed by treatment of the formed intermediate with the dione of Formula 3 in the presence of a base such as triethylamine (Scheme 4). This coupling is carried out by methods known in the art (or by slight modification of these methods): for example, see E. Haslam *Tetrahedron* (1980), 36, 2409–2433.

Scheme 4

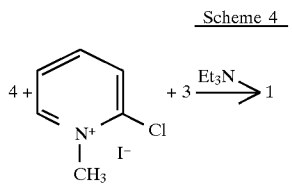

Compounds of Formula 4 (X is other than CH or N) can be readily prepared by treatment of thioketals of Formula 5 with bromine or an appropriate Lewis acid such as tellurium tetrachloride (Scheme 5). This rearrangement is carried out by methods known in the art (or by slight modification of these methods): for example, see Plumbo, G. et al. *Tetrahedron* (1991), 47, 4187–4194; Plumbo, G. et al. *Synthesis* (1991), 223–224; Plumbo G. et al. *Tetrahedron* (1986), 42, 2369–2376; Satoh, J. et al. *J. Chem. Amer. Soc., Chem. Commun.* (1985), 1645–1646; Tani, H. et al. *Chem. Lett.* (1990), 1323–1326; Nickon, A. et al. *J. Org. Chem.* (1985), 50, 4218–4226.

Scheme 5

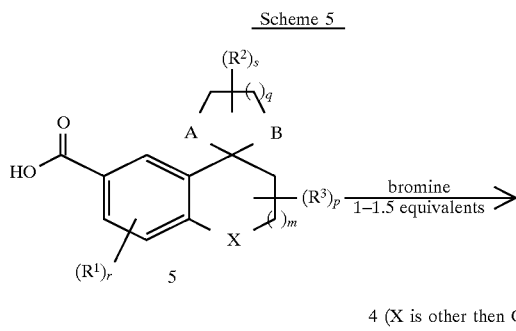

Scheme 6 illustrates the preparation of compounds of Formula 4 (X is CH) whereby a thioketal of Formula 5 (X is $CH_2$) is treated with 2–3 equivalents of bromine. This rearrangement is carried out by methods known in the art (or by slight modification of these methods): for example, see Plumbo, G. et al. *Tetrahedron* (1991), 47, 4187–4194; Satoh, J. et al. *J. Chem. Amer. Soc., Chem. Commun.* (1985), 1645–1646; Tani, H. et al. *Chem. Lett.* (1990), 1323–1326; Nickon, A. et al. *J. Org. Chem.* (1985), 50, 4218–4226.

Scheme 6

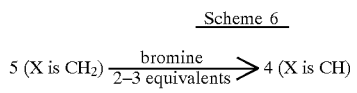

Scheme 7 illustrates the preparation of acids of Formula 5 (n is 0 when X is $S(O)_n$) whereby a phenyl bromide of Formula 6 (n is 0 when X is $S(O)_n$) is treated with n-butyllithium (or magnesium), and the lithium salt (or the Grignard reagent) generated in situ is then reacted with carbon dioxide followed by acidification with an acid such as hydrochloric acid. This conversion is carried out by general methods known in the art; see for example, M. A. Ogliaruso et al., *Synthesis of Carboxylic Acids, Esters and Their Derivatives*, pp 27–28, John Wiley & Sons; A. J. Bridges, et al., *J. Org. Chem.* (1990), 55 (2), 773; C. Franke, et al., *Angew. Chem. Int. Ed.* (1969), 8, 68. In some instances, the incorporation of protection/deprotection sequences or functional group interconversions into the synthesis will aid in obtaining the desired products. The use and choice of the protecting groups will be apparent to one skilled in chemical synthesis (see, for example, Green, T. W.; Wuts, P. G. M., Protective Groups in Organic Synthesis, 2nd ed.; Wiley: New York, 1991).

Scheme 7

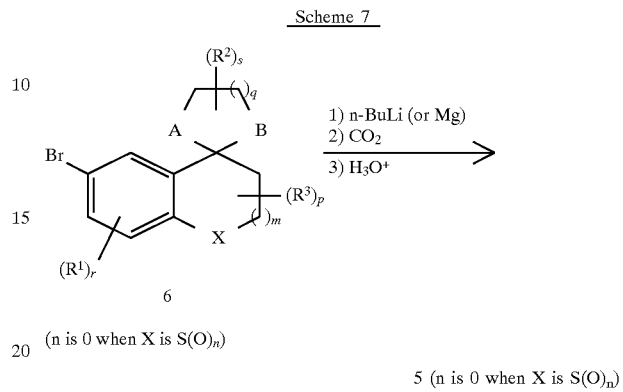

Scheme 8 illustrates the preparation of phenyl bromides of Formula 6 (n is 0 when X is $S(O)_n$) whereby a ketone of Formula 7 (n is 0 when X is $S(O)_n$) is reacted with $HO(CH_2)_qSH$ or $HS(CH_2)_qSH$ in the presence of a Lewis acid such as $BF_3$ etherate in an inert organic solvent such as dichloromethane. This conversion is carried out by general methods known in the art; see for example, T. W. Greene, et al., *Protective Groups in Organic Synthesis*, John Wiley & Sons, Inc., pp 133–140.

Scheme 8

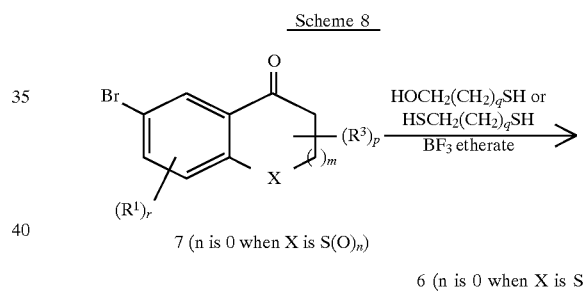

Scheme 9 illustrates the preparation of carboxylic acids of Formula 5 (n is 1 or 2 when X is $S(O)_n$) whereby a ketone of Formula 8 (n is 1 or 2 when X is $S(O)_n$) is reacted with $HO(CH_2)_qSH$ or $HS(CH_2)_qSH$ in the presence of a Lewis acid such as $BF_3$ etherate in an inert organic solvent such as dichloromethane. This conversion is carried out by general methods known in the art; see for example, T. W. Greene, et al., *Protective Groups in Organic Synthesis*, John Wiley & Sons, Inc., pp 133–140.

Scheme 9

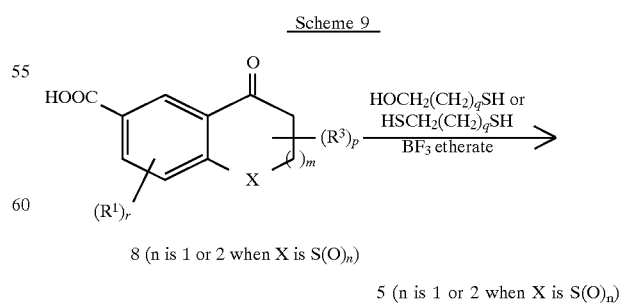

The ketones of Formula 7 can also be prepared by general methods known in the art (or by slight modification of these methods); see, for example, W. Flemming, et al., *Chem. Ber.*

(1925), 58, 1612; I. W. J. Still, et al., *Can. J Chem.* (1976), 54, 453–470; V. J. Traynelis, et al., *J. Org. Chem.* (1961), 26, 2728; I. Nasuno, et al., WO 94/08988; F. Camps, et al., *J. Heterocycl. Chem.* (1985), 22(5), p. 1421; T. S. Rao, et al., *Indian J. Chem. B.* (1985), 24(11), p. 1159; S. Ghosh, et al., *Tetrahedron* (1989), 45(5), p. 1441; A. Danan, et al., *Synthesis-Stuttgart* (1991), (1I), p. 879; P. Magnus, et al., *J. Chem. Soc. Chem. Comm.* (1991), (7), p. 544; A. Padwa, et al., *J. Org. Chem.* (1989), 54(12), p. 2862; S. A. Ali, et al., *J. Org. Chem.* (1979), 44, p. 4213; J. Blake, et al., *J. Am. Chem. Soc.* (1966), 88, p. 4061; M. Mori, et al., *J. Chem. Soc. Chem. Comm.* (1990), (18), p. 1222; S. Kano, et al., *J. Chem. Soc., Perkin. Trans.* 1 (1980), p. 2105; A. F. Bekhli, et al., *Khim Geterotsikl. Soedin.* (1975), p. 1118; W. S. Johnson, et al., *J. Am. Chem. Soc.* (1949), 71, p. 1901; J. A. Hirsch, et al., *J. Org. Chem.* (1974), 39(14), p. 2044; F. G. Mann, et al., *J. Chem. Soc.* (1957), p. 4166; A. C. Jain, et al., *Indian. J. Chem. B* (1987), 26(2), p. 136; G. Ariamala, et al., *Tet. Lett.* (1988), 29(28), p. 3487; B. Loubinoux, et al., *Tet. Lett.* (1992), 33(16), p. 2145; S. Cabiddu, et al., *J. Organomet. Chem.* (1989), 366(1–2), p. 1; R. HasenKamp, et al., *Chem. Ber.* (1980), 113, p. 1708; D. A. Pulman, et al., *J. Chem. Soc. Perkin. Trans.* 1 (1973), p. 410; W. C. Lumma, et al., *J. Org. Chem.* (1969), 34, p. 1566; P. D. Clark, et al., *Can. J. Chem.* (1982), 60(3), p. 243.

The dicarbonyl compounds of Formula 3 are either commercially available or can be prepared by general methods known in the art (or by slight modification of these methods): for example, see D. Cartwright, et al., EP 0283261-B 1; J. Dangelo, et al., *Tet. Lett.* (1991), 32(26), p. 3063; T. Okado, et al., *J. Org. Chem.* (1977), 42, p. 1163; B. E. Maryanoff, et al., *J. Am. Chem Soc.* (1975), 97, p. 2718; E. Er, et al., *Helv. Chim. Acta.* (1992), 75(7), p. 2265; Y. D. Vankar, et al., *Tet. Lett.,* (1987), 28(5), p. 551; C. S. Pak, et al., *Tet. Lett.* (1991), 32(42), p. 6011; I. Nishiguchi, et al., *Chem. Lett.* (1981), p. 551; B. Eistert, et al., *Liebigs Ann. Chem.* (1962), 659, p. 64; N. K. Hamer, *Tet. Lett.* (1986), 27(19), p. 2167; M. Sato, et al., *Heterocycles* (1987), 26(10), p. 2611; A. Murray, et al., *Tet. Lett.* (1995), 36(2), p. 291; K. S. Kochhar, et al., *Tet. Lett.* (1984), 25(18), p. 1871; M. Sato, et al., *Tetrahedron* (1991), 47(30), p. 5689; M. Sato, et al., *Chem. Pharm. Bull.* (1990), 38(1), p. 94; T. Meal, U.S. Pat. No. 4,931,570; T. Muel, et al., U.S. Pat. No. 5,093,503.

Compounds of General Formula Ie can be readily prepared by one skilled in the art by using the reactions and techniques described in Schemes 10–12 of this section.

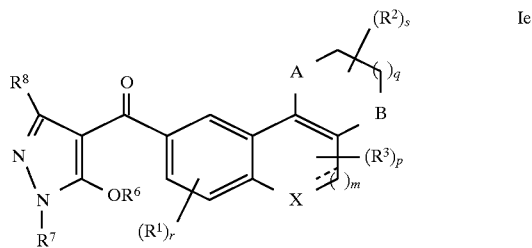

Scheme 10 illustrates the preparation of compounds of Formula Ie ($R^6$=H). whereby an ester of Formula 9 or its isomer 9a is reacted with a base such as triethylamine in the presence of a catalytic amount of cyanide source (e.g., acetone cyanohydrin or potassium cyanide). This rearrangement is carried out by methods known in the art (or by slight modification of these methods): for example, see W. J. Michaely, EP 369,803.

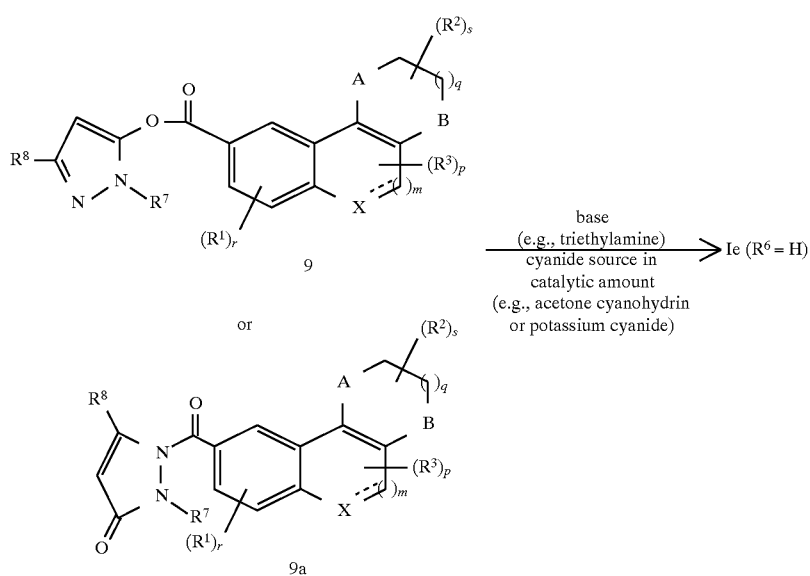

Scheme 10

Compounds of Formula 9 or 9a can be prepared by reacting the acid of Formula 4 with N-methyl-2-chloropyridinium iodide, followed by treatment of the formed intermediate with the hydroxypyrazole of Formula 10 in the presence of a base such as triethylamine (Scheme 11). This coupling is carried out by methods known in the art (or by slight modification of these methods): for example, see E. Haslam *Tetrahedron* (1980), 36, 2409–2433.

Scheme 11

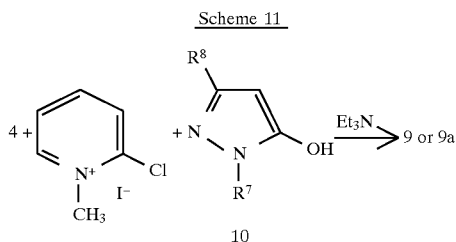

Esters of Formula 9 or amides of Formula 9a can also be prepared by reacting a hydroxypyrazole of Formula 10 with an acid chloride of Formula 2 in the presence of a slight mole excess of a base such as triethylamine in an inert organic solvent such as acetonitrile, methylene chloride or toluene at temperatures between 0° C. and 110° C. (Scheme 12). This type of coupling is carried out by methods known in the art (or by slight modification of these methods): for example, see W. J. Michaely, EP 369,803.

Scheme 12

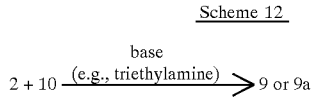

Compounds of General Formula If can be readily prepared by one skilled in the art by using the reactions and techniques described in Schemes 13–16 of this section.

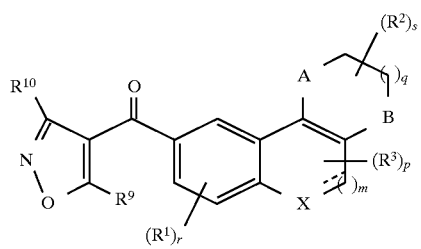

Scheme 13 illustrates the preparation of compounds of Formula If whereby a compound of Formula 11 is reacted with a salt of hydroxylamine such as hydroxylamine hydrochloride in the presence of a base or acid acceptor such as triethylamine or sodium acetate. The substituents of the immediate products may be further modified if appropriate. This cyclization is carried out by methods known in the art (or by slight modification of these methods): for example, see P. A. Cain, et al., EP 560,483; C. J. Pearson, et al., EP 636,622.

Scheme 13

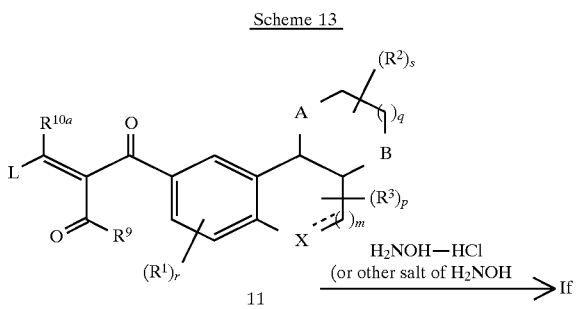

wherein
L is a leaving group such as $C_1$–$C_4$ alkoxy (e.g., $OC_2H_5$) or N,N-dialkylamino (e.g., dimethyl amino) $R^{10a}$ is H, $C_2$–$C_6$ alkoxycarbonyl, $C_2$–$C_6$ haloalkoxycarbonyl or $CONH_2$ Scheme 14 illustrates the preparation of compounds of Formula 11 whereby a compound of Formula 12 is reacted with a reagent of Formula 13 or Formula 14. This conversion is carried out by methods known in the art (or by slight modification of these methods): for example, see P. A. Cain, et al., EP 560,483; C. J. Pearson, et al., EP 636,622.

Scheme 14

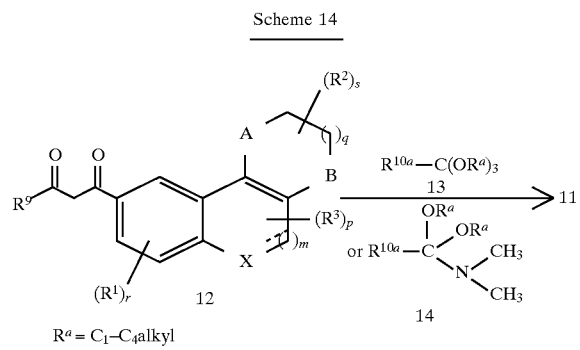

$R^a$ = $C_1$–$C_4$alkyl

Scheme 15 illustrates the preparation of compounds of Formula 12 whereby an ester of Formula 15 is decarboxylated in the presence of a catalyst, such as p-toluenesulfonic acid, in an inert solvent such as toluene. This conversion is carried out by methods known in the art (or by slight modification of these methods): for example, see P. A. Cain, et al., EP 560,483; C. J. Pearson, et al., EP 636,622.

Scheme 15

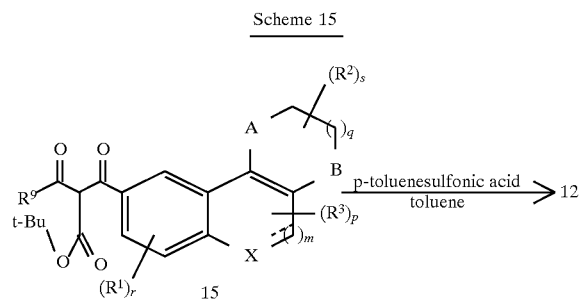

Esters of Formula 15 can be prepared by reacting the metal salt of a compound of Formula 16 with an acid chloride of Formula 2 (Scheme 16). This type of coupling is known in the art: for example see P. A. Cain, et al., EP 560,483; C. J. Pearson, et al., EP 636,622.

Scheme 16

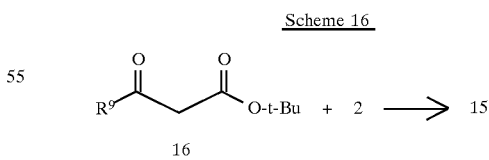

Scheme 17 illustrates the preparation of compounds of Formula Ig whereby a compound of Formula 2 is reacted with a compound of Formula 17 in the presence of a base such as triethylamine, potassium carbonate, sodium hydride or $Mg(OEt)_2$ in an inert organic solvent such as diethyl ether, tetrahydrofuran, N,N-dimethylformamide, dichloromethane or acetonitrile.

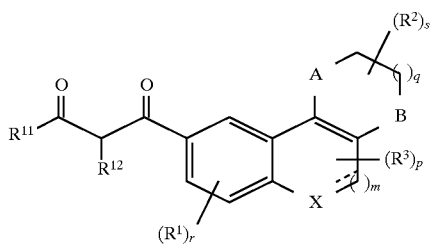

This conversion is carried out by methods known in the art (or slight modification of these methods); for example, see J. W. Ashmore, EP 213,892 and P. A. Cain, EP 496,631 A1.

Scheme 17

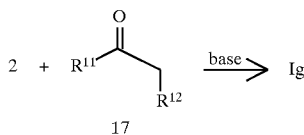

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet.

EXAMPLE 1

Step A: Preparation of 2,3-dihydro-7,10-dimethyl-5H-1,4-dithiino[2,3-c][1]benzothiopyran-9-carboxylic acid A mixture of 0.62 g of 2,3-dihydro-5,8-dimethylspiro[4H-1-benzothiopyran-4,2'-[1,3]dithiolane]-6-carboxylic acid in 200 mL of chloroform was cooled to 0° C. To this mixture was added a solution of 0.38 g of bromine in 20 mL of chloroform dropwise. The resulting mixture was stirred overnight at room temperature. To this reaction mixture was added 10% aqueous sodium thiosulfate. The organic layer was separated and dried over MgSO$_4$, filtered, and concentrated under reduced pressure to dryness. The resulting residue was crystallized from 1-chlorobutane to gave 0.29 g of the title compound of Step A as a purple solid melting at 250° C. (dec.). $^1$H NMR (CDCl$_3$): δ 2.35 (s, 3H), 2.70 (s, 3H), 3.05 (m, 2H), 3.39 (br s, 2H), 3.41 (m, 2H), 7.66 (s, 1H).

Step B: Preparation of 3-oxo-1-cyclohexen-1-yl 2,3-dihydro-7,10-dimethyl-5H- 1,4-dithiino[2,3-c][1]benzothiopyran-9-carboxylate To a mixture of 0.78 g of the title compound of Step A in 35 mL of methylene chloride was added 0.66 mL of oxalyl chloride (purchased from Aldrich Chemical Co.) and 2 drops of N,N-dimethylformamide. The mixture was refluxed for 2 h and was then concentrated under reduced pressure to dryness. The resulting residue was redissolved in 30 mL of methylene chloride and the solution was evaporated to dryness again. Another 30 mL of methylene chloride was added to the residue and the solution was cooled to about 0° C. To this solution was added 0.31 g of 1,3-cyclohexanedione (purchased from Aldrich Chemical Co.) followed by addition of 1.0 mL of triethylamine. The mixture was stirred overnight while warming to room temperature. Saturated aqueous sodium bicarbonate was then added to the reaction mixture and the mixture was extracted with methylene chloride. The combined organic extracts were dried over MgSO$_4$, filtered, and concentrated under reduced pressure to dryness. Chromatography of the crude product on silica gel eluting with a mixture of hexanes:ethyl acetate (8:1 and then 4:1) yielded 0.58 g of the title compound of Step B as a yellow solid melting at 120°–126° C. $^1$H NMR (CDCl$_3$): δ 2.15 (m, 2H), 2.36 (s, 3H), 2.46 (t, 2H), 2.66 (t, 2H), 2.67 (s, 3H), 3.07 (m, 2H), 3.24 (br s, 2H), 3.41 (m, 2H), 6.00 (s, 1H), 7.60 (s, 1H).

Step C: Preparation of 2-[(2,3-dihydro-7,10-dimethyl-5H-1,4-dithiino[2,3-c][1]benzothiopyran-9-yl)carbonyl]-1,3-cyclohexanedione To a mixture of 0.55 g of the title compound of Step B in 25 mL of anhydrous acetonitrile and 5 mL of methylene chloride was added 0.34 mL of triethylamine, 2 drops of acetone cyanohydrin (purchased from Aldrich Chemical Co.), and 5 mg of potassium cyanide. The mixture was allowed to stir at room temperature overnight. An additional 5 mg of potassium cyanide was added and the reaction mixture was stirred at 50° C. for 48 h. The mixture was concentrated under reduced pressure to dryness and to the resulting residue was added dilute hydrochloric acid of pH 1. The mixture was extracted with ethyl acetate, and the combined organic extracts were dried over MgSO$_4$, filtered, and concentrated under reduced pressure to afford 0.36 g of the title compound of Step C, a compound of this invention, as a brown solid melting at 95° C. (dec.). $^1$H NMR (CDCl$_3$): δ 2.06 (m, 2H), 2.30 (s, 3H), 2.34 (s, 3H), 2.30–2.90 (m, 4H), 3.05 (m, 2H), 3.22 (br s, 2H), 3.39 (m, 2H), 6.70 (s, 1H).

EXAMPLE 2

Step A: Preparation of 2,3-dihydro-5,8-dimethylspiro[4H-1-benzothiopyran4,2'-[1,3]dithiolane]-6-carboxylic acid 1,1-dioxide To a mixture of 0.60 g of 3,4-dihydro-5,8-dimethyl4-oxo-2H-1-benzothiopyran-6-carboxylic acid 1,1-dioxide in 30 mL of methylene chloride was added 0.24 mL of 1,2- ethanedithiol (purchased from Aldrich Chemical Co.) and 0.35 mL of boron trifluoride diethyl etherate (purchased from Janssen Chimica). The mixture was refluxed overnight and then concentrated under reduced pressure to dryness. To the resulting residue was added 10 mL of dilute hydrochloric acid of pH 1. The mixture was extracted with ethyl acetate, and the combined organic extracts were dried over MgSO$_4$, filtered, and concentrated under reduced pressure to afford 0.62 g of the title compound of Step A as an orange solid which had a melting point >250° C. $^1$H NMR ((CD$_3$)$_2$SO): δ 2.65 (s, 3H), 2.77 (s, 3H), 2.94 (m, 2H), 3.55–3.80 (m, 6H), 7.50 (s, 1H).

Step B: Preparation of 2,3-dihydro-7,10-dimethyl-5H-1,4-dithiino[2,3-c][1]benzothiopyran-9-carboxylic acid 6,6-dioxide A mixture of 0.50 g of the title compound of Step A in 200 mL of chloroform was cooled to 0° C. To this mixture was added a solution of 0.45 g of bromine in 35 mL of chloroform dropwise. The mixture was stirred at room temperature for 2 h and then 10% aqueous sodium thiosulfate solution was added. The organic layer was separated and dried over MgSO$_4$, filtered, and concentrated under reduced pressure to dryness. The resulting residue was crystallized from 1-chlorobutane to yield 0.41 g of the title compound of Step B as a solid melting at 145° C. (dec.). $^1$H NMR (CDCl$_3$): δ 2.49 (s, 3H), 2.56 (s, 3H), 3.11 (br s, 2H), 3.48 (m, 2H), 4.24 (br s, 2H), 7.57 (s, 1H).

Step C: Preparation of 2,3-dihydro-7,10-dimethyl-5H-1,4-dithiino[2,3-c][1]benzothiopyran-9-carbonyl chloride 6,6-dioxide To a mixture of 0.40 g of the title compound of Step B in 15 mL of methylene chloride was added 0.31 mL of oxalyl chloride (purchased from Aldrich Chemical Co.) and 2 drops of N,N-dimethylformamide. The mixture was refluxed for 2 h and was then concentrated under reduced pressure to dryness. To the resulting residue was added 20 mL of methylene chloride and this solution was evaporated to dryness again. Another 20 mL of methylene chloride was added to the residue to provide the title compound of Step C as a methylene chloride solution. This solution was divided into two equal portions and was used as a starting material for both step D in Example 2 and step A in Example 4.

Step D: Preparation of 3-oxo-1-cyclohexen-1-yl 2,3-dihydro-7,10-dimethyl-5H-1,4-dithiino[2,3-c][1]benzothiopyran-9-carboxylate 6,6-dioxide A solution of the title compound of Step C in 10 mL of methylene chloride was cooled to 0° C. To this solution was added 0.07 g of 1,3-cyclohexanedione (purchased from Aldrich Chemical Co.) followed by addition of 0.24 mL of triethylamine. The mixture was stirred overnight at room temperature, and then saturated aqueous sodium bicarbonate solution was added. The mixture was extracted with methylene chloride, and the combined organic extracts were dried over MgSO$_4$, filtered, and concentrated under reduced pressure to dryness. Chromatography of the crude product on silica gel eluting with a mixture of hexanes:ethyl acetate (5:1 and then 2:1) yielded 0.14 g of the title compound of Step D as a semi-solid. $^1$H NMR (CDCl$_3$): δ 2.15 (m, 2H), 2.49 (t, 2H), 2.62 (s, 3H), 2.69 (m, 2H), 2.72 (s, 3H), 3.11 (m, 2H), 3.52 (m, 2H), 3.85 (s, 2H), 6.02 (s, 1H), 7.68 (s, 1H).

Step E: Preparation of 2-[(2,3-dihydro-7,10-dimethyl-6,6-dioxido-5H-1,4-dithiino[2,3-c][1]benzothiopyran-9-yl)carbonyl]-1,3-cyclohexanedione To a mixture of 0.14 g of the title compound of Step D in 10 mL of anhydrous acetonitrile was added 0.08 mL of triethylamine, 2 drops of acetone cyanohydrin (purchased from Aldrich Chemical Co.), and 5 mg of potassium cyanide. The mixture was allowed to stir at room temperature overnight. The mixture was concentrated under reduced pressure to dryness. To the resulting residue was added water and the mixture was acidified to pH 2 with concentrated hydrochloric acid and extracted with ethyl acetate. The combined organic extracts were dried over MgSO$_4$, filtered, and concentrate under reduced pressure to afford 0.12 g of the title compound of Step E, a compound of this invention, as a solid melting at 208°–213° C. $^1$H NMR (CDCl$_3$): δ 2.05 (m, 2H), 2.28 (s, 3H), 2.45 (m, 2H), 2.64 (s, 3H), 2.79 (m, 2H), 3.11 (m, 2 H), 3.50 (m, 2H), 3.85 (s, 2H), 6.82 (s, 1H).

EXAMPLE 3

Step A: Preparation of 7-bromo-5,8-dimethyltetralone

To a solution of 15.0 g of 5,8-dimethyltetralone (purchased from Wiley Organics) in 250 mL of methylene chloride was added 28.7 g of aluminum chloride (purchased from Aldrich Chemical Co.). The mixture was cooled to 0° C. and then a solution of 15.2 g bromine in 90 mL of methylene chloride was added dropwise. After the mixture was stirred at room temperature for 2 h, it was cooled to 0° C. and then approximately 200 g of ice was added. The resulting mixture was filtered. The organic layer was separated and was washed with 1N aqueous sodium hydroxide, dried over MgSO$_4$, filtered, and concentrated under reduced pressure. The resulting solid was crystallized from 1-chlorobutane to give 21.8 g of the title compound of Step A as a solid melting at 64°–68° C. $^1$H NMR (CDCl$_3$): δ 2.11 (m, 2H), 2.25 (s, 3H), 2.64 (t, 2H), 2.66 (s, 3H), 2.77 (t, 2H), 7.53 (s, 1H).

Step B: Preparation of 7'-bromo-3',4'-dihydro-5',8'-dimethlspiro[1,3-dithiolane-2,1'(2'H)-naphthalene]

To a mixture of 20.0 g of the title compound of Step A in 500 mL of methylene chloride was added 11.2 mL of 1,2-ethanedithiol (purchased from Aldrich Chemical Co.) and 17.0 mL of boron trifluoride diethyl etherate (purchased from Janssen Chimica). The mixture was stirred at room temperature for 3 h. To this reaction mixture was added 15% aqueous sodium hydroxide and the resulting mixture was extracted with methylene chloride. The combined organic extracts were dried over MgSO$_4$, filtered, and concentrated under reduced pressure to afford 20.2 g of the title compound of Step B as a white solid melting at 164°–165° C. $^1$H NMR (CDCl$_3$): δ 1.98 (m, 2H), 2.15 (s, 3H), 2.38 (m, 2H), 2.58 (t, 2H), 2.78 (s, 3H), 3.40–3.60 (m, 4H), 7.35 (s, 1H).

Step C: Preparation of 3',4'-dihydro-5',8'-dimethylspiro[1,3-dithiolane-2,1'(2'H)-naphthalene]-7'-carboxylic acid A solution of 12.7 g of the title compound of Step B in 300 mL of tetrahydrofuran under a nitrogen atmosphere was cooled to −78° C. To this solution was slowly added 19.2 mL of a 2.5M solution of n-butyllithium in hexane (purchased from Aldrich Chemical Co.). The reaction mixture was maintained below −60° C. during the addition of n-butyllithium and stirring 30 min after addition was complete. The mixture was then cooled to −78° C. and 35.0 g of crushed dry ice was added. The resulting mixture was stirred and allowed to warm to room over 1.5 h. The mixture was then concentrated under reduced pressure, and to the resulting residue was added 300 mL of water. The mixture was then cooled to 0° C., acidified to pH 2 with concentrated hydrochloric acid, and extracted with ethyl acetate. The combined organic layers were dried over MgSO$_4$, filtered, and concentrated under reduced pressure. The resulting solid was crystallized from 1-chlorobutane to gave 3.2 g of the title compound of Step C as a white solid melting at 215° C. (dec.). $^1$H NMR ((CD$_3$)$_2$SO): δ 1.90 (m, 2H), 2.16 (s, 3H), 2.34 (m, 2H), 2.61 (t, 2H), 2.75 (s, 3H), 3.40–3.70 (m, 4H), 7.29 (s, 1H), 12.75 (br s, 1 H).

Step D: Preparation of 2,3-dihydro-7,10-dimethylnaphtho[1,2-b]-1,4-dithiin-9-carboxylic acid To a mixture of 1.2 g of the title compound of Step C in 150 mL of chloroform was added a solution of 0.76 g of bromine in 30 mL of chloroform dropwise. The mixture was stirred overnight at room temperature. To this reaction mixture was then added 10% aqueous sodium thiosulfate. The organic layer was separated, dried over MgSO$_4$, filtered, and concentrated under reduced pressure to dryness. The resulting solid was crystallized from 1-chlorobutane to gave 0.65 g of the title compound of Step D as a yellow solid melting at 205° C. (dec.). $^1$H NMR ((CD$_3$)$_2$SO): δ 2.58 (s, 3H), 2.91 (s, 3H), 2.98 (m, 2H), 3.49 (m, 2H), 7.47 (d, 1H), 7.49 (s, 1H), 7.73 (d, 1H).

Step E: Preparation of 3-oxo-1-cyclohexen-1-yl 2,3-dihydro-7,10-dimethylnaphtho[1,2-b]-1,4-dithiin-9-carboxylate To a mixture of 0.40 g of the title compound of Step D in 25 mL of tetrahydrofuran was added 0.34 mL of oxalyl chloride (purchased from Aldrich Chemical Co.) and 2 drops of N,N-dimethylformamide. The mixture was refluxed for 2 h and was then concentrated under reduced pressure to dryness. To the resulting residue was added 25 mL of tetrahydrofuran and evaporated to dryness again. Another 25 mL of tetrahydrofuran was added to the residue and the solution was cooled to about 0° C. To this mixture was added 0.16 g of 1,3-cyclohexanedione (purchased from Aldrich Chemical Co.) followed by addition of 0.52 mL of triethylamine. The mixture was stirred overnight at room temperature. To the reaction mixture was added saturated aqueous sodium bicarbonate and the mixture was extracted with methylene chloride. The combined organic extracts were dried over MgSO$_4$, filtered, and concentrated under reduced pressure to dryness. Chromatography of the crude product on silica gel eluting with a mixture of hexanes:ethyl acetate (8:1 and then 4:1) yielded 0.21 g of the title compound of Step E as a yellow solid melting at 126°–130° C. $^1$H NMR (CDCl$_3$): δ 2.18 (m, 2H), 2.49 (t, 2H), 2.64 (s, 3H), 2.72 (t, 2H), 2.90 (t, 2H), 3.06 (s, 3H), 3.52 (t, 2H), 6.07 (s, 1H), 7.50 (d, 1H), 7.62 (s, 1H), 7.70 (d, 1H).

Step F: Preparation of 2-[(2,3-dihydro-7,10-dimethylnaphtho[1,2-b]-1,4-dithiin-9-yl)carbonyl]-1,3-cyclohexanedione To a mixture of 0.20 g of the title compound of Step E in 20 mL of anhydrous acetonitrile was added 0.14 mL of triethylamine, 2 drops of acetone cyanohydrin (purchased from Aldrich Chemical Co.), and 5 mg of potassium cyanide. The mixture was refluxed overnight and then concentrated under reduced pressure to dryness. To the resulting residue was added dilute hydrochloric acid of pH 1 and the mixture was extracted with ethyl acetate. The combined organic extracts were dried over MgSO$_4$, filtered, and concentrated under reduced pressure. The resulting solid was crystallized from 1-chlorobutane to gave 0.16 g of the title compound of Step F, a compound of this invention, as a semi-solid. $^1$H NMR (CDCl$_3$): δ 2.05 (m, 2H), 2.44 (m, 2H), 2.59 (s, 3H), 2.84 (s, 3H), 2.75–3.00 (m, 4H), 3.47 (t, 2H), 6.93 (s, 1H), 7.44 (d, 1H), 7.68 (d, 1H).

EXAMPLE 4

Step A: Preparation of 1-ethyl-1H-pyrazol-5-yl 2,3-dihydro-7,10-dimethyl-5H-1,4-dithiino[2,3-c][1]benzothiopyran-9-carboxylate 6,6-dioxide A solution of the title compound of Step C of Example 2 in 10 mL of methylene chloride was cooled to 0° C. To this solution was added 0.22 g of 1-ethyl-1H-pyrazol-5-ol followed by addition of 0.24 mL of triethylamine. The mixture was stirred overnight while warming to room temperature. To the reaction mixture was added saturated aqueous sodium bicarbonate. The mixture was extracted with methylene chloride, and the combined organic extracts were dried over MgSO$_4$, filtered, and concentrated under reduced pressure to dryness. Chromatography of the crude product on silica gel eluting with a mixture of hexanes : ethyl acetate (5:1 and then 2:1) yielded 0.04 g of the title compound of Step A as a semi-solid. $^1$H NMR (CDCl$_3$): δ 1.45 (t, 3H), 2.67 (s, 3H), 2.75 (s, 3H), 3.14 (m, 2H), 3.54 (m, 2H), 3.89 (s, 2H), 4.12 (m, 2H), 6.22 (s, 1H), 7.49 (s, 1 H), 7.81 (s, 1H).

Step B: Preparation of (2,3-dihydro-7,10-dimethyl-6,.6-dioxido-5H-1,4-dithiino[2,3-c][1]benzothiopyran-9-yl)(1-ethyl-5-hydroxy-1H-pyrazol-4-yl)methanone To a mixture of 0.04 g of the title compound of Step A in 5 mL of anhydrous acetonitrile was added 0.02 mL of triethylamine, 2 drops of acetone cyanohydrin (purchased from Aldrich Chemical Co.), and 5 mg of potassium cyanide. The mixture was allowed to stir at room temperature overnight. The mixture was then concentrated under reduced pressure to dryness and water was added to the resulting residue. The mixture was acidified to pH 2 with concentrated hydrochloric acid. The mixture was then extracted with ethyl acetate and the combined organic extracts were dried over MgSO$_4$, filtered, and concentrated under reduced pressure to afford 0.04 g of the title compound of Step B, a compound of this invention, as a solid melting at 210°–216° C. $^1$H NMR (CDCl$_3$): δ 1.46 (t, 3H), 2.44 (s, 3H), 2.70 (s, 3H), 3.11 (m, 2H), 3.53 (m, 2H), 3.86 (s, 2H), 4.07 (m, 2H), 7.20 (s, 1H), 7.35 (s, 1H).

By the procedures described herein together with methods known in the art, the following compounds of Tables 1 to 8 can be prepared.

TABLE 1

| $R^{5a}$ | $R^{5b}$ | $R^4$ | $R^{1a}$ | $R^{1b}$ | A | B |
|---|---|---|---|---|---|---|
| wherein X is CH$_2$ | | | | | | |
| H | H | OH | H | H | O | S |
| H | CH$_3$ | OH | H | H | O | S |
| CH$_3$ | CH$_3$ | OH | H | H | O | S |
| H | H | OH | CH$_3$ | H | O | S |
| H | CH$_3$ | OH | CH$_3$ | H | O | S |
| CH$_3$ | CH$_3$ | OH | CH$_3$ | H | O | S |
| H | H | OH | CH$_3$ | CH$_3$ | O | S |
| H | CH$_3$ | OH | CH$_3$ | CH$_3$ | O | S |
| CH$_3$ | CH$_3$ | OH | CH$_3$ | CH$_3$ | O | S |
| H | H | OH | CH$_3$ | Cl | O | S |
| H | CH$_3$ | OH | CH$_3$ | Cl | O | S |
| CH$_3$ | CH$_3$ | OH | CH$_3$ | Cl | O | S |
| H | H | OH | Cl | H | O | S |
| H | CH$_3$ | OH | Cl | H | O | S |
| CH$_3$ | CH$_3$ | OH | Cl | H | O | S |
| H | H | OH | Cl | CH$_3$ | O | S |
| H | CH$_3$ | OH | Cl | CH$_3$ | O | S |
| CH$_3$ | CH$_3$ | OH | Cl | CH$_3$ | O | S |
| H | H | OH | H | H | O | SO$_2$ |
| H | CH$_3$ | OH | H | H | O | SO$_2$ |
| CH$_3$ | CH$_3$ | OH | H | H | O | SO$_2$ |
| H | H | OH | CH$_3$ | H | O | SO$_2$ |
| H | CH$_3$ | OH | CH$_3$ | H | O | SO$_2$ |
| CH$_3$ | CH$_3$ | OH | CH$_3$ | H | O | SO$_2$ |
| H | H | OH | CH$_3$ | CH$_3$ | O | SO$_2$ |
| H | CH$_3$ | OH | CH$_3$ | CH$_3$ | O | SO$_2$ |
| CH$_3$ | CH$_3$ | OH | CH$_3$ | CH$_3$ | O | SO$_2$ |
| H | H | OH | CH$_3$ | Cl | O | SO$_2$ |
| H | CH$_3$ | OH | CH$_3$ | Cl | O | SO$_2$ |
| CH$_3$ | CH$_3$ | OH | CH$_3$ | Cl | O | SO$_2$ |
| H | H | OH | Cl | H | O | SO$_2$ |
| H | CH$_3$ | OH | Cl | H | O | SO$_2$ |
| CH$_3$ | CH$_3$ | OH | Cl | H | O | SO$_2$ |
| H | H | OH | Cl | CH$_3$ | O | SO$_2$ |

TABLE 1-continued

| R5a | R5b | R4 | R1a | R1b | A | B |
|---|---|---|---|---|---|---|
| H | CH₃ | OH | Cl | CH₃ | O | SO₂ |
| CH₃ | CH₃ | OH | Cl | CH₃ | O | SO₂ |
| H | H | OH | H | H | S | S |
| H | CH₃ | OH | H | H | S | S |
| CH₃ | CH₃ | OH | H | H | S | S |
| H | H | OH | CH₃ | H | S | S |
| H | CH₃ | OH | CH₃ | H | S | S |
| CH₃ | CH₃ | OH | CH₃ | H | S | S |
| H | H | OH | CH₃ | CH₃ | S | S |
| H | CH₃ | OH | CH₃ | CH₃ | S | S |
| CH₃ | CH₃ | OH | CH₃ | CH₃ | S | S |
| H | H | OH | CH₃ | Cl | S | S |
| H | CH₃ | OH | CH₃ | Cl | S | S |
| CH₃ | CH₃ | OH | CH₃ | Cl | S | S |
| H | H | OH | Cl | H | S | S |
| H | CH₃ | OH | Cl | H | S | S |
| CH₃ | CH₃ | OH | Cl | H | S | S |
| H | H | OH | Cl | CH₃ | S | S |
| H | CH₃ | OH | Cl | CH₃ | S | S |
| CH₃ | CH₃ | OH | Cl | CH₃ | S | S |
| H | H | OH | H | H | SO₂ | SO₂ |
| H | CH₃ | OH | H | H | SO₂ | SO₂ |
| CH₃ | CH₃ | OH | H | H | SO₂ | SO₂ |
| H | H | OH | CH₃ | H | SO₂ | SO₂ |
| H | CH₃ | OH | CH₃ | H | SO₂ | SO₂ |
| CH₃ | CH₃ | OH | CH₃ | H | SO₂ | SO₂ |
| H | H | OH | CH₃ | CH₃ | SO₂ | SO₂ |
| H | CH₃ | OH | CH₃ | CH₃ | SO₂ | SO₂ |
| CH₃ | CH₃ | OH | CH₃ | CH₃ | SO₂ | SO₂ |
| H | H | OH | CH₃ | Cl | SO₂ | SO₂ |
| H | CH₃ | OH | CH₃ | Cl | SO₂ | SO₂ |
| CH₃ | CH₃ | OH | CH₃ | Cl | SO₂ | SO₂ |
| H | H | OH | Cl | H | SO₂ | SO₂ |
| H | CH₃ | OH | Cl | H | SO₂ | SO₂ |
| CH₃ | CH₃ | OH | Cl | H | SO₂ | SO₂ |
| H | H | OH | Cl | CH₃ | SO₂ | SO₂ |
| H | CH₃ | OH | Cl | CH₃ | SO₂ | SO₂ |
| CH₃ | CH₃ | OH | Cl | CH₃ | SO₂ | SO₂ |
| H | H | OS(O)₂(4-CH₃Ph) | CH₃ | CH₃ | O | S |
| H | CH₃ | OS(O)₂(4-CH₃Ph) | CH₃ | CH₃ | O | S |
| CH₃ | CH₃ | OS(O)₂(4-CH₃Ph) | CH₃ | CH₃ | O | S |
| H | H | OS(O)₂(4-CH₃Ph) | CH₃ | CH₃ | O | SO₂ |
| H | CH₃ | OS(O)₂(4-CH₃Ph) | CH₃ | CH₃ | O | SO₂ |
| CH₃ | CH₃ | OS(O)₂(4-CH₃Ph) | CH₃ | CH₃ | O | SO₂ |
| H | H | OS(O)₂(4-CH₃Ph) | CH₃ | CH₃ | S | S |
| H | CH₃ | OS(O)₂(4-CH₃Ph) | CH₃ | CH₃ | S | S |
| CH₃ | CH₃ | OS(O)₂(4-CH₃Ph) | CH₃ | CH₃ | S | S |
| H | H | OS(O)₂(4-CH₃Ph) | CH₃ | CH₃ | SO₂ | SO₂ |
| H | CH₃ | OS(O)₂(4-CH₃Ph) | CH₃ | CH₃ | SO₂ | SO₂ |
| CH₃ | CH₃ | OS(O)₂(4-CH₃Ph) | CH₃ | CH₃ | SO₂ | SO₂ |
| H | H | OC(=O)(4-CH₃Ph) | CH₃ | CH₃ | O | S |
| H | CH₃ | OC(=O)(4-CH₃Ph) | CH₃ | CH₃ | O | S |
| CH₃ | CH₃ | OC(=O)(4-CH₃Ph) | CH₃ | CH₃ | O | S |
| H | H | OC(=O)(4-CH₃Ph) | CH₃ | CH₃ | O | SO₂ |
| H | CH₃ | OC(=O)(4-CH₃Ph) | CH₃ | CH₃ | O | SO₂ |
| CH₃ | CH₃ | OC(=O)(4-CH₃Ph) | CH₃ | CH₃ | O | SO₂ |
| H | H | OC(=O)(4-CH₃Ph) | CH₃ | CH₃ | S | S |
| H | CH₃ | OC(=O)(4-CH₃Ph) | CH₃ | CH₃ | S | S |
| CH₃ | CH₃ | OC(=O)(4-CH₃Ph) | CH₃ | CH₃ | S | S |
| H | H | OC(=O)(4-CH₃Ph) | CH₃ | CH₃ | SO₂ | SO₂ |
| H | CH₃ | OC(=O)(4-CH₃Ph) | CH₃ | CH₃ | SO₂ | SO₂ |
| CH₃ | CH₃ | OC(=O)(4-CH₃Ph) | CH₃ | CH₃ | SO₂ | SO₂ | wherein X is SO₂

| R5a | R5b | R4 | R1a | R1b | A | B |
|---|---|---|---|---|---|---|
| H | H | OH | H | H | O | S |
| H | H | OH | H | H | O | S |
| H | CH₃ | OH | H | H | O | S |
| CH₃ | CH₃ | OH | H | H | O | S |
| H | H | OH | CH₃ | H | O | S |
| H | CH₃ | OH | CH₃ | H | O | S |
| CH₃ | CH₃ | OH | CH₃ | H | O | S |
| H | H | OH | CH₃ | CH₃ | O | S |
| H | CH₃ | OH | CH₃ | CH₃ | O | S |
| CH₃ | CH₃ | OH | CH₃ | CH₃ | O | S |
| H | H | OH | CH₃ | Cl | O | S |
| H | CH₃ | OH | CH₃ | Cl | O | S |
| CH₃ | CH₃ | OH | CH₃ | Cl | O | S |
| H | H | OH | Cl | H | O | S |
| H | CH₃ | OH | Cl | H | O | S |
| CH₃ | CH₃ | OH | Cl | H | O | S |
| H | H | OH | Cl | CH₃ | O | S |
| H | CH₃ | OH | Cl | CH₃ | O | S |
| CH₃ | CH₃ | OH | Cl | CH₃ | O | S |
| H | H | OH | H | H | O | SO₂ |
| H | CH₃ | OH | H | H | O | SO₂ |
| CH₃ | CH₃ | OH | H | H | O | SO₂ |
| H | H | OH | CH₃ | H | O | SO₂ |
| H | CH₃ | OH | CH₃ | H | O | SO₂ |
| CH₃ | CH₃ | OH | CH₃ | H | O | SO₂ |
| H | H | OH | CH₃ | CH₃ | O | SO₂ |
| H | CH₃ | OH | CH₃ | CH₃ | O | SO₂ |
| CH₃ | CH₃ | OH | CH₃ | CH₃ | O | SO₂ |
| H | H | OH | CH₃ | Cl | O | SO₂ |
| H | CH₃ | OH | CH₃ | Cl | O | SO₂ |
| CH₃ | CH₃ | OH | CH₃ | Cl | O | SO₂ |
| H | H | OH | Cl | H | O | SO₂ |
| H | CH₃ | OH | Cl | H | O | SO₂ |
| CH₃ | CH₃ | OH | Cl | H | O | SO₂ |
| H | H | OH | Cl | CH₃ | O | SO₂ |
| H | CH₃ | OH | Cl | CH₃ | O | SO₂ |
| CH₃ | CH₃ | OH | Cl | CH₃ | O | SO₂ |
| H | H | OH | H | H | S | S |
| H | CH₃ | OH | H | H | S | S |
| CH₃ | CH₃ | OH | H | H | S | S |
| H | H | OH | CH₃ | H | S | S |
| H | CH₃ | OH | CH₃ | H | S | S |
| CH₃ | CH₃ | OH | CH₃ | H | S | S |
| H | H | OH | CH₃ | CH₃ | S | S |
| H | CH₃ | OH | CH₃ | CH₃ | S | S |
| CH₃ | CH₃ | OH | CH₃ | CH₃ | S | S |
| H | H | OH | CH₃ | Cl | S | S |
| H | CH₃ | OH | CH₃ | Cl | S | S |
| CH₃ | CH₃ | OH | CH₃ | Cl | S | S |
| H | H | OH | Cl | H | S | S |
| H | CH₃ | OH | Cl | H | S | S |
| CH₃ | CH₃ | OH | Cl | H | S | S |
| H | H | OH | Cl | CH₃ | S | S |
| H | CH₃ | OH | Cl | CH₃ | S | S |
| CH₃ | CH₃ | OH | Cl | CH₃ | S | S |
| H | H | OH | H | H | SO₂ | SO₂ |
| H | CH₃ | OH | H | H | SO₂ | SO₂ |
| CH₃ | CH₃ | OH | H | H | SO₂ | SO₂ |
| H | H | OH | CH₃ | H | SO₂ | SO₂ |
| H | CH₃ | OH | CH₃ | H | SO₂ | SO₂ |
| CH₃ | CH₃ | OH | CH₃ | H | SO₂ | SO₂ |
| H | H | OH | CH₃ | CH₃ | SO₂ | SO₂ |
| H | CH₃ | OH | CH₃ | CH₃ | SO₂ | SO₂ |
| CH₃ | CH₃ | OH | CH₃ | CH₃ | SO₂ | SO₂ |
| H | H | OH | CH₃ | Cl | SO₂ | SO₂ |
| H | CH₃ | OH | CH₃ | Cl | SO₂ | SO₂ |
| CH₃ | CH₃ | OH | CH₃ | Cl | SO₂ | SO₂ |
| H | H | OH | Cl | H | SO₂ | SO₂ |
| H | CH₃ | OH | Cl | H | SO₂ | SO₂ |
| CH₃ | CH₃ | OH | Cl | H | SO₂ | SO₂ |
| H | H | OH | Cl | CH₃ | SO₂ | SO₂ |
| H | CH₃ | OH | Cl | CH₃ | SO₂ | SO₂ |
| CH₃ | CH₃ | OH | Cl | CH₃ | SO₂ | SO₂ |

TABLE 1-continued

| R5a | R5b | R4 | R1a | R1b | A | B |
|---|---|---|---|---|---|---|
| CH3 | CH3 | OH | Cl | CH3 | SO2 | SO2 |
| H | H | OS(O)2(4-CH3Ph) | CH3 | CH3 | O | S |
| H | CH3 | OS(O)2(4-CH3Ph) | CH3 | CH3 | O | S |
| CH3 | CH3 | OS(O)2(4-CH3Ph) | CH3 | CH3 | O | S |
| H | H | OS(O)2(4-CH3Ph) | CH3 | CH3 | O | SO2 |
| H | CH3 | OS(O)2(4-CH3Ph) | CH3 | CH3 | O | SO2 |
| CH3 | CH3 | OS(O)2(4-CH3Ph) | CH3 | CH3 | O | SO2 |
| H | H | OS(O)2(4-CH3Ph) | CH3 | CH3 | S | S |
| H | CH3 | OS(O)2(4-CH3Ph) | CH3 | CH3 | S | S |
| CH3 | CH3 | OS(O)2(4-CH3Ph) | CH3 | CH3 | S | S |
| H | H | OS(O)2(4-CH3Ph) | CH3 | CH3 | SO2 | SO2 |
| H | CH3 | OS(O)2(4-CH3Ph) | CH3 | CH3 | SO2 | SO2 |
| CH3 | CH3 | OS(O)2(4-CH3Ph) | CH3 | CH3 | SO2 | SO2 |
| H | H | OC(=O)(4-CH3Ph) | CH3 | CH3 | O | S |
| H | CH3 | OC(=O)(4-CH3Ph) | CH3 | CH3 | O | S |
| CH3 | CH3 | OC(=O)(4-CH3Ph) | CH3 | CH3 | O | S |
| H | H | OC(=O)(4-CH3Ph) | CH3 | CH3 | O | SO2 |
| H | CH3 | OC(=O)(4-CH3Ph) | CH3 | CH3 | O | SO2 |
| CH3 | CH3 | OC(=O)(4-CH3Ph) | CH3 | CH3 | O | SO2 |
| H | H | OC(=O)(4-CH3Ph) | CH3 | CH3 | S | S |
| H | CH3 | OC(=O)(4-CH3Ph) | CH3 | CH3 | S | S |
| CH3 | CH3 | OC(=O)(4-CH3Ph) | CH3 | CH3 | S | S |
| H | H | OC(=O)(4-CH3Ph) | CH3 | CH3 | SO2 | SO2 |
| H | CH3 | OC(=O)(4-CH3Ph) | CH3 | CH3 | SO2 | SO2 |
| CH3 | CH3 | OC(=O)(4-CH3Ph) | CH3 | CH3 | SO2 | SO2 |

TABLE 2

| R5a | R5b | R4 | R1a | R1b | A | B |
|---|---|---|---|---|---|---|
| wherein X is CH | | | | | | |
| H | H | OH | H | H | O | S |
| H | CH3 | OH | H | H | O | S |
| CH3 | CH3 | OH | H | H | O | S |
| H | H | OH | CH3 | H | O | S |
| H | CH3 | OH | CH3 | H | O | S |
| CH3 | CH3 | OH | CH3 | H | O | S |
| H | H | OH | CH3 | CH3 | O | S |
| H | CH3 | OH | CH3 | CH3 | O | S |
| CH3 | CH3 | OH | CH3 | CH3 | O | S |
| H | H | OH | CH3 | Cl | O | S |
| H | CH3 | OH | CH3 | Cl | O | S |
| CH3 | CH3 | OH | CH3 | Cl | O | S |
| H | H | OH | Cl | H | O | S |
| H | CH3 | OH | Cl | H | O | S |
| CH3 | CH3 | OH | Cl | H | O | S |
| H | H | OH | Cl | CH3 | O | S |
| H | CH3 | OH | Cl | CH3 | O | S |
| CH3 | CH3 | OH | Cl | CH3 | O | S |
| H | H | OH | H | H | O | SO2 |
| H | CH3 | OH | H | H | O | SO2 |
| CH3 | CH3 | OH | H | H | O | SO2 |
| H | H | OH | CH3 | H | O | SO2 |
| H | CH3 | OH | CH3 | H | O | SO2 |

TABLE 2-continued

| R5a | R5b | R4 | R1a | R1b | A | B |
|---|---|---|---|---|---|---|
| CH3 | CH3 | OH | CH3 | H | O | SO2 |
| H | H | OH | CH3 | CH3 | O | SO2 |
| H | CH3 | OH | CH3 | CH3 | O | SO2 |
| CH3 | CH3 | OH | CH3 | CH3 | O | SO2 |
| H | H | OH | CH3 | Cl | O | SO2 |
| H | CH3 | OH | CH3 | Cl | O | SO2 |
| CH3 | CH3 | OH | CH3 | Cl | O | SO2 |
| H | H | OH | Cl | H | O | SO2 |
| H | CH3 | OH | Cl | H | O | SO2 |
| CH3 | CH3 | OH | Cl | H | O | SO2 |
| H | H | OH | Cl | CH3 | O | SO2 |
| H | CH3 | OH | Cl | CH3 | O | SO2 |
| CH3 | CH3 | OH | Cl | CH3 | O | SO2 |
| H | H | OH | H | H | S | S |
| H | CH3 | OH | H | H | S | S |
| CH3 | CH3 | OH | H | H | S | S |
| H | H | OH | CH3 | H | S | S |
| H | CH3 | OH | CH3 | H | S | S |
| CH3 | CH3 | OH | CH3 | H | S | S |
| H | H | OH | CH3 | CH3 | S | S |
| H | CH3 | OH | CH3 | CH3 | S | S |
| CH3 | CH3 | OH | CH3 | CH3 | S | S |
| H | H | OH | CH3 | Cl | S | S |
| H | CH3 | OH | CH3 | Cl | S | S |
| CH3 | CH3 | OH | CH3 | Cl | S | S |
| H | H | OH | Cl | H | S | S |
| H | CH3 | OH | Cl | H | S | S |
| CH3 | CH3 | OH | Cl | H | S | S |
| H | H | OH | Cl | CH3 | S | S |
| H | CH3 | OH | Cl | CH3 | S | S |
| CH3 | CH3 | OH | Cl | CH3 | S | S |
| H | H | OH | H | H | SO2 | SO2 |
| H | CH3 | OH | H | H | SO2 | SO2 |
| CH3 | CH3 | OH | H | H | SO2 | SO2 |
| H | H | OH | CH3 | H | SO2 | SO2 |
| H | CH3 | OH | CH3 | H | SO2 | SO2 |
| CH3 | CH3 | OH | CH3 | H | SO2 | SO2 |
| H | H | OH | CH3 | CH3 | SO2 | SO2 |
| H | CH3 | OH | CH3 | CH3 | SO2 | SO2 |
| CH3 | CH3 | OH | CH3 | CH3 | SO2 | SO2 |
| H | H | OH | CH3 | Cl | SO2 | SO2 |
| H | CH3 | OH | CH3 | Cl | SO2 | SO2 |
| CH3 | CH3 | OH | CH3 | Cl | SO2 | SO2 |
| H | H | OH | Cl | H | SO2 | SO2 |
| H | CH3 | OH | Cl | H | SO2 | SO2 |
| CH3 | CH3 | OH | Cl | H | SO2 | SO2 |
| H | H | OH | Cl | CH3 | SO2 | SO2 |
| H | CH3 | OH | Cl | CH3 | SO2 | SO2 |
| CH3 | CH3 | OH | Cl | CH3 | SO2 | SO2 |
| H | H | OS(O)2(4-CH3Ph) | CH3 | CH3 | O | S |
| H | CH3 | OS(O)2(4-CH3Ph) | CH3 | CH3 | O | S |
| CH3 | CH3 | OS(O)2(4-CH3Ph) | CH3 | CH3 | O | S |
| H | H | OS(O)2(4-CH3Ph) | CH3 | CH3 | O | SO2 |
| H | CH3 | OS(O)2(4-CH3Ph) | CH3 | CH3 | O | SO2 |
| CH3 | CH3 | OS(O)2(4-CH3Ph) | CH3 | CH3 | O | SO2 |
| H | H | OS(O)2(4-CH3Ph) | CH3 | CH3 | S | S |
| H | CH3 | OS(O)2(4-CH3Ph) | CH3 | CH3 | S | S |
| CH3 | CH3 | OS(O)2(4-CH3Ph) | CH3 | CH3 | S | S |
| H | H | OS(O)2(4-CH3Ph) | CH3 | CH3 | SO2 | SO2 |
| H | CH3 | OS(O)2(4-CH3Ph) | CH3 | CH3 | SO2 | SO2 |
| CH3 | CH3 | OS(O)2(4-CH3Ph) | CH3 | CH3 | SO2 | SO2 |
| H | H | OC(=O)(4-CH3Ph) | CH3 | CH3 | O | S |
| H | CH3 | OC(=O)(4-CH3Ph) | CH3 | CH3 | O | S |
| CH3 | CH3 | OC(=O)(4-CH3Ph) | CH3 | CH3 | O | S |
| H | H | OC(=O)(4-CH3Ph) | CH3 | CH3 | O | SO2 |
| H | CH3 | OC(=O)(4-CH3Ph) | CH3 | CH3 | O | SO2 |
| CH3 | CH3 | OC(=O)(4-CH3Ph) | CH3 | CH3 | O | SO2 |

TABLE 2-continued

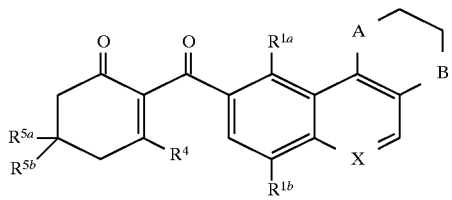

| $R^{5a}$ | $R^{5b}$ | $R^4$ | $R^{1a}$ | $R^{1b}$ | A | B |
|---|---|---|---|---|---|---|
| H | H | OC(=O)(4-CH$_3$Ph) | CH$_3$ | CH$_3$ | S | S |
| H | CH$_3$ | OC(=O)(4-CH$_3$Ph) | CH$_3$ | CH$_3$ | S | S |
| CH$_3$ | CH$_3$ | OC(=O)(4-CH$_3$Ph) | CH$_3$ | CH$_3$ | S | S |
| H | H | OC(=O)(4-CH$_3$Ph) | CH$_3$ | CH$_3$ | SO$_2$ | SO$_2$ |
| H | CH$_3$ | OC(=O)(4-CH$_3$Ph) | CH$_3$ | CH$_3$ | SO$_2$ | SO$_2$ |
| CH$_3$ | CH$_3$ | OC(=O)(4-CH$_3$Ph) | CH$_3$ | CH$_3$ | SO$_2$ | SO$_2$ |
| wherein X is N |
| H | H | OH | H | H | O | S |
| H | CH$_3$ | OH | H | H | O | S |
| CH$_3$ | CH$_3$ | OH | H | H | O | S |
| H | H | OH | CH$_3$ | H | O | S |
| H | CH$_3$ | OH | CH$_3$ | H | O | S |
| CH$_3$ | CH$_3$ | OH | CH$_3$ | H | O | S |
| H | H | OH | CH$_3$ | CH$_3$ | O | S |
| H | CH$_3$ | OH | CH$_3$ | CH$_3$ | O | S |
| CH$_3$ | CH$_3$ | OH | CH$_3$ | CH$_3$ | O | S |
| H | H | OH | CH$_3$ | Cl | O | S |
| H | CH$_3$ | OH | CH$_3$ | Cl | O | S |
| CH$_3$ | CH$_3$ | OH | CH$_3$ | Cl | O | S |
| H | H | OH | Cl | H | O | S |
| H | CH$_3$ | OH | Cl | H | O | S |
| CH$_3$ | CH$_3$ | OH | Cl | H | O | S |
| H | H | OH | Cl | CH$_3$ | O | S |
| H | CH$_3$ | OH | Cl | CH$_3$ | O | S |
| CH$_3$ | CH$_3$ | OH | Cl | CH$_3$ | O | S |
| H | H | OH | H | H | O | SO$_2$ |
| H | CH$_3$ | OH | H | H | O | SO$_2$ |
| CH$_3$ | CH$_3$ | OH | H | H | O | SO$_2$ |
| H | H | OH | CH$_3$ | H | O | SO$_2$ |
| H | CH$_3$ | OH | CH$_3$ | H | O | SO$_2$ |
| CH$_3$ | CH$_3$ | OH | CH$_3$ | H | O | SO$_2$ |
| H | H | OH | CH$_3$ | CH$_3$ | O | SO$_2$ |
| H | CH$_3$ | OH | CH$_3$ | CH$_3$ | O | SO$_2$ |
| CH$_3$ | CH$_3$ | OH | CH$_3$ | CH$_3$ | O | SO$_2$ |
| H | H | OH | CH$_3$ | Cl | O | SO$_2$ |
| H | CH$_3$ | OH | CH$_3$ | Cl | O | SO$_2$ |
| CH$_3$ | CH$_3$ | OH | CH$_3$ | Cl | O | SO$_2$ |
| H | H | OH | Cl | H | O | SO$_2$ |
| H | CH$_3$ | OH | Cl | H | O | SO$_2$ |
| CH$_3$ | CH$_3$ | OH | Cl | H | O | SO$_2$ |
| H | H | OH | Cl | CH$_3$ | O | SO$_2$ |
| H | CH$_3$ | OH | Cl | CH$_3$ | O | SO$_2$ |
| CH$_3$ | CH$_3$ | OH | Cl | CH$_3$ | O | SO$_2$ |
| H | H | OH | H | H | S | S |
| H | CH$_3$ | OH | H | H | S | S |
| CH$_3$ | CH$_3$ | OH | H | H | S | S |
| H | H | OH | CH$_3$ | H | S | S |
| H | CH$_3$ | OH | CH$_3$ | H | S | S |
| CH$_3$ | CH$_3$ | OH | CH$_3$ | H | S | S |
| H | H | OH | CH$_3$ | CH$_3$ | S | S |
| H | CH$_3$ | OH | CH$_3$ | CH$_3$ | S | S |
| CH$_3$ | CH$_3$ | OH | CH$_3$ | CH$_3$ | S | S |
| H | H | OH | CH$_3$ | Cl | S | S |
| H | CH$_3$ | OH | CH$_3$ | Cl | S | S |
| CH$_3$ | CH$_3$ | OH | CH$_3$ | Cl | S | S |
| H | H | OH | Cl | H | S | S |
| H | CH$_3$ | OH | Cl | H | S | S |
| CH$_3$ | CH$_3$ | OH | Cl | H | S | S |
| H | H | OH | Cl | CH$_3$ | S | S |
| H | CH$_3$ | OH | Cl | CH$_3$ | S | S |
| CH$_3$ | CH$_3$ | OH | Cl | CH$_3$ | S | S |
| H | H | OH | H | H | SO$_2$ | SO$_2$ |
| H | CH$_3$ | OH | H | H | SO$_2$ | SO$_2$ |
| CH$_3$ | CH$_3$ | OH | H | H | SO$_2$ | SO$_2$ |
| H | H | OH | CH$_3$ | H | SO$_2$ | SO$_2$ |
| H | CH$_3$ | OH | CH$_3$ | H | SO$_2$ | SO$_2$ |

TABLE 2-continued

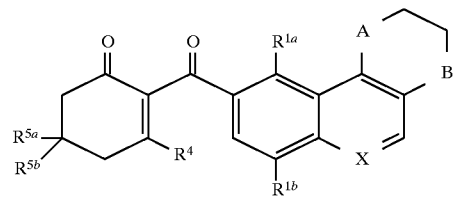

| $R^{5a}$ | $R^{5b}$ | $R^4$ | $R^{1a}$ | $R^{1b}$ | A | B |
|---|---|---|---|---|---|---|
| CH$_3$ | CH$_3$ | OH | CH$_3$ | H | SO$_2$ | SO$_2$ |
| H | H | OH | CH$_3$ | CH$_3$ | SO$_2$ | SO$_2$ |
| H | CH$_3$ | OH | CH$_3$ | CH$_3$ | SO$_2$ | SO$_2$ |
| CH$_3$ | CH$_3$ | OH | CH$_3$ | CH$_3$ | SO$_2$ | SO$_2$ |
| H | H | OH | CH$_3$ | Cl | SO$_2$ | SO$_2$ |
| H | CH$_3$ | OH | CH$_3$ | Cl | SO$_2$ | SO$_2$ |
| CH$_3$ | CH$_3$ | OH | CH$_3$ | Cl | SO$_2$ | SO$_2$ |
| H | H | OH | Cl | H | SO$_2$ | SO$_2$ |
| H | CH$_3$ | OH | Cl | H | SO$_2$ | SO$_2$ |
| CH$_3$ | CH$_3$ | OH | Cl | H | SO$_2$ | SO$_2$ |
| H | H | OH | Cl | CH$_3$ | SO$_2$ | SO$_2$ |
| H | CH$_3$ | OH | Cl | CH$_3$ | SO$_2$ | SO$_2$ |
| CH$_3$ | CH$_3$ | OH | Cl | CH$_3$ | SO$_2$ | SO$_2$ |
| H | H | OS(O)$_2$(4-CH$_3$Ph) | CH$_3$ | CH$_3$ | O | S |
| H | CH$_3$ | OS(O)$_2$(4-CH$_3$Ph) | CH$_3$ | CH$_3$ | O | S |
| CH$_3$ | CH$_3$ | OS(O)$_2$(4-CH$_3$Ph) | CH$_3$ | CH$_3$ | O | S |
| H | H | OS(O)$_2$(4-CH$_3$Ph) | CH$_3$ | CH$_3$ | O | SO$_2$ |
| H | CH$_3$ | OS(O)$_2$(4-CH$_3$Ph) | CH$_3$ | CH$_3$ | O | SO$_2$ |
| CH$_3$ | CH$_3$ | OS(O)$_2$(4-CH$_3$Ph) | CH$_3$ | CH$_3$ | O | SO$_2$ |
| H | H | OS(O)$_2$(4-CH$_3$Ph) | CH$_3$ | CH$_3$ | S | S |
| H | CH$_3$ | OS(O)$_2$(4-CH$_3$Ph) | CH$_3$ | CH$_3$ | S | S |
| CH$_3$ | CH$_3$ | OS(O)$_2$(4-CH$_3$Ph) | CH$_3$ | CH$_3$ | S | S |
| H | H | OS(O)$_2$(4-CH$_3$Ph) | CH$_3$ | CH$_3$ | SO$_2$ | SO$_2$ |
| H | CH$_3$ | OS(O)$_2$(4-CH$_3$Ph) | CH$_3$ | CH$_3$ | SO$_2$ | SO$_2$ |
| CH$_3$ | CH$_3$ | OS(O)$_2$(4-CH$_3$Ph) | CH$_3$ | CH$_3$ | SO$_2$ | SO$_2$ |
| H | H | OC(=O)(4-CH$_3$Ph) | CH$_3$ | CH$_3$ | O | S |
| H | CH$_3$ | OC(=O)(4-CH$_3$Ph) | CH$_3$ | CH$_3$ | O | S |
| CH$_3$ | CH$_3$ | OC(=O)(4-CH$_3$Ph) | CH$_3$ | CH$_3$ | O | S |
| H | H | OC(=O)(4-CH$_3$Ph) | CH$_3$ | CH$_3$ | O | SO$_2$ |
| H | CH$_3$ | OC(=O)(4-CH$_3$Ph) | CH$_3$ | CH$_3$ | O | SO$_2$ |
| CH$_3$ | CH$_3$ | OC(=O)(4-CH$_3$Ph) | CH$_3$ | CH$_3$ | O | SO$_2$ |
| H | H | OC(=O)(4-CH$_3$Ph) | CH$_3$ | CH$_3$ | S | S |
| H | CH$_3$ | OC(=O)(4-CH$_3$Ph) | CH$_3$ | CH$_3$ | S | S |
| CH$_3$ | CH$_3$ | OC(=O)(4-CH$_3$Ph) | CH$_3$ | CH$_3$ | S | S |
| H | H | OC(=O)(4-CH$_3$Ph) | CH$_3$ | CH$_3$ | SO$_2$ | SO$_2$ |
| H | CH$_3$ | OC(=O)(4-CH$_3$Ph) | CH$_3$ | CH$_3$ | SO$_2$ | SO$_2$ |
| CH$_3$ | CH$_3$ | OC(=O)(4-CH$_3$Ph) | CH$_3$ | CH$_3$ | SO$_2$ | SO$_2$ |

TABLE 3

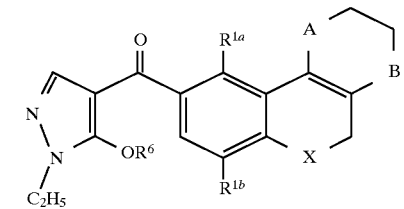

| $R^6$ | $R^{1a}$ | $R^{1b}$ | A | B |
|---|---|---|---|---|
| wherein X is CH$_2$ |
| H | H | H | O | S |
| H | CH$_3$ | H | O | S |
| H | CH$_3$ | CH$_3$ | O | S |
| H | CH$_3$ | Cl | O | S |
| H | Cl | H | O | S |
| H | Cl | CH$_3$ | O | S |
| H | H | H | O | SO$_2$ |
| H | CH$_3$ | H | O | SO$_2$ |
| H | CH$_3$ | CH$_3$ | O | SO$_2$ |
| H | CH$_3$ | Cl | O | SO$_2$ |

TABLE 3-continued

[Structure: pyrazole-C(=O)-phenyl with R1a, R1b, OR6, C2H5, and fused ring with A, B, X]

| R6 | R1a | R1b | A | B |
|---|---|---|---|---|
| H | Cl | H | O | SO2 |
| H | Cl | CH3 | O | SO2 |
| H | H | H | S | S |
| H | CH3 | H | S | S |
| H | CH3 | CH3 | S | S |
| H | CH3 | Cl | S | S |
| H | Cl | H | S | S |
| H | Cl | CH3 | S | S |
| H | H | H | SO2 | SO2 |
| H | CH3 | H | SO2 | SO2 |
| H | CH3 | CH3 | SO2 | SO2 |
| H | CH3 | Cl | SO2 | SO2 |
| H | Cl | H | SO2 | SO2 |
| H | Cl | CH3 | SO2 | SO2 |
| S(O)2(4-CH3Ph) | CH3 | CH3 | O | S |
| S(O)2(4-CH3Ph) | CH3 | CH3 | O | SO2 |
| S(O)2(4-CH3Ph) | CH3 | CH3 | S | S |
| S(O)2(4-CH3Ph) | CH3 | CH3 | SO2 | SO2 |
| C(=O)(4-CH3Ph) | CH3 | CH3 | O | S |
| C(=O)(4-CH3Ph) | CH3 | CH3 | O | SO2 |
| C(=O)(4-CH3Ph) | CH3 | CH3 | S | S |
| C(=O)(4-CH3Ph) | CH3 | CH3 | SO2 | SO2 |
| C(=O)CH(CH3)2 | CH3 | CH3 | O | S |
| C(=O)CH(CH3)2 | CH3 | CH3 | O | SO2 |
| C(=O)CH(CH3)2 | CH3 | CH3 | S | S |
| C(=O)CH(CH3)2 | CH3 | CH3 | SO2 | SO2 |
| C(=O)OCH(CH3)2 | CH3 | CH3 | O | S |
| C(=O)OCH(CH3)2 | CH3 | CH3 | O | SO2 |
| C(=O)OCH(CH3)2 | CH3 | CH3 | S | S |
| C(=O)OCH(CH3)2 | CH3 | CH3 | SO2 | SO2 |
| C(=O)OCH3 | CH3 | CH3 | O | S |
| C(=O)OCH3 | CH3 | CH3 | O | SO2 |
| C(=O)OCH3 | CH3 | CH3 | S | S |
| C(=O)OCH3 | CH3 | CH3 | SO2 | SO2 | wherein X is SO2

| R6 | R1a | R1b | A | B |
|---|---|---|---|---|
| H | H | H | O | S |
| H | CH3 | H | O | S |
| H | CH3 | CH3 | O | S |
| H | CH3 | Cl | O | S |
| H | Cl | H | O | S |
| H | Cl | CH3 | O | S |
| H | H | H | O | SO2 |
| H | CH3 | H | O | SO2 |
| H | CH3 | CH3 | O | SO2 |
| H | CH3 | Cl | O | SO2 |
| H | Cl | H | O | SO2 |
| H | Cl | CH3 | O | SO2 |
| H | H | H | S | S |
| H | CH3 | H | S | S |
| H | CH3 | CH3 | S | S |
| H | CH3 | Cl | S | S |
| H | Cl | H | S | S |
| H | Cl | CH3 | S | S |
| H | H | H | SO2 | SO2 |
| H | CH3 | H | SO2 | SO2 |
| H | CH3 | CH3 | SO2 | SO2 |
| H | CH3 | Cl | SO2 | SO2 |
| H | Cl | H | SO2 | SO2 |
| H | Cl | CH3 | SO2 | SO2 |
| S(O)2(4-CH3Ph) | CH3 | CH3 | O | S |
| S(O)2(4-CH3Ph) | CH3 | CH3 | O | SO2 |
| S(O)2(4-CH3Ph) | CH3 | CH3 | S | S |
| S(O)2(4-CH3Ph) | CH3 | CH3 | SO2 | SO2 |
| C(=O)(4-CH3Ph) | CH3 | CH3 | O | S |
| C(=O)(4-CH3Ph) | CH3 | CH3 | O | SO2 |
| C(=O)(4-CH3Ph) | CH3 | CH3 | S | S |
| C(=O)(4-CH3Ph) | CH3 | CH3 | SO2 | SO2 |
| C(=O)CH(CH3)2 | CH3 | CH3 | O | S |
| C(=O)CH(CH3)2 | CH3 | CH3 | O | SO2 |
| C(=O)CH(CH3)2 | CH3 | CH3 | S | S |
| C(=O)CH(CH3)2 | CH3 | CH3 | SO2 | SO2 |
| C(=O)OCH(CH3)2 | CH3 | CH3 | O | S |
| C(=O)OCH(CH3)2 | CH3 | CH3 | O | SO2 |
| C(=O)OCH(CH3)2 | CH3 | CH3 | S | S |
| C(=O)OCH(CH3)2 | CH3 | CH3 | SO2 | SO2 |
| C(=O)OCH3 | CH3 | CH3 | O | S |
| C(=O)OCH3 | CH3 | CH3 | O | SO2 |
| C(=O)OCH3 | CH3 | CH3 | S | S |
| C(=O)OCH3 | CH3 | CH3 | SO2 | SO2 |

TABLE 4

[Structure: pyrazole-C(=O)-phenyl with R1a, R1b, OR6, C2H5, and fused ring with A, B, X]

| R6 | R1a | R1b | A | B |
|---|---|---|---|---| wherein X is CH

| R6 | R1a | R1b | A | B |
|---|---|---|---|---|
| H | H | H | O | S |
| H | CH3 | H | O | S |
| H | CH3 | CH3 | O | S |
| H | CH3 | Cl | O | S |
| H | Cl | H | O | S |
| H | Cl | CH3 | O | S |
| H | H | H | O | SO2 |
| H | CH3 | H | O | SO2 |
| H | CH3 | CH3 | O | SO2 |
| H | CH3 | Cl | O | SO2 |
| H | Cl | H | O | SO2 |
| H | Cl | CH3 | O | SO2 |
| H | H | H | S | S |
| H | CH3 | H | S | S |
| H | CH3 | CH3 | S | S |
| H | CH3 | Cl | S | S |
| H | Cl | H | S | S |
| H | Cl | CH3 | S | S |
| H | H | H | SO2 | SO2 |
| H | CH3 | H | SO2 | SO2 |
| H | CH3 | CH3 | SO2 | SO2 |
| H | CH3 | Cl | SO2 | SO2 |
| H | Cl | H | SO2 | SO2 |
| H | Cl | CH3 | SO2 | SO2 |
| S(O)2(4-CH3Ph) | CH3 | CH3 | O | S |
| S(O)2(4-CH3Ph) | CH3 | CH3 | O | SO2 |
| S(O)2(4-CH3Ph) | CH3 | CH3 | S | S |
| S(O)2(4-CH3Ph) | CH3 | CH3 | SO2 | SO2 |
| C(=O)(4-CH3Ph) | CH3 | CH3 | O | S |
| C(=O)(4-CH3Ph) | CH3 | CH3 | O | SO2 |
| C(=O)(4-CH3Ph) | CH3 | CH3 | S | S |
| C(=O)(4-CH3Ph) | CH3 | CH3 | SO2 | SO2 |

TABLE 4-continued

[Structure: pyrazole with N-C₂H₅, OR⁶, C(=O) connected to benzene ring with R¹ᵃ, R¹ᵇ substituents, fused to ring with A, B, X]

| R⁶ | R¹ᵃ | R¹ᵇ | A | B |
|---|---|---|---|---|
| C(=O)CH(CH₃)₂ | CH₃ | CH₃ | O | S |
| C(=O)CH(CH₃)₂ | CH₃ | CH₃ | O | SO₂ |
| C(=O)CH(CH₃)₂ | CH₃ | CH₃ | S | S |
| C(=O)CH(CH₃)₂ | CH₃ | CH₃ | SO₂ | SO₂ |
| C(=O)OCH(CH₃)₂ | CH₃ | CH₃ | O | S |
| C(=O)OCH(CH₃)₂ | CH₃ | CH₃ | O | SO₂ |
| C(=O)OCH(CH₃)₂ | CH₃ | CH₃ | S | S |
| C(=O)OCH(CH₃)₂ | CH₃ | CH₃ | SO₂ | SO₂ |
| C(=O)OCH₃ | CH₃ | CH₃ | O | S |
| C(=O)OCH₃ | CH₃ | CH₃ | O | SO₂ |
| C(=O)OCH₃ | CH₃ | CH₃ | S | S |
| C(=O)OCH₃ | CH₃ | CH₃ | SO₂ | SO₂ |
| wherein X is N | | | | |
| H | H | H | O | S |
| H | CH₃ | H | O | S |
| H | CH₃ | CH₃ | O | S |
| H | CH₃ | Cl | O | S |
| H | Cl | H | O | S |
| H | Cl | CH₃ | O | S |
| H | H | H | O | SO₂ |
| H | CH₃ | H | O | SO₂ |
| H | CH₃ | CH₃ | O | SO₂ |
| H | CH₃ | Cl | O | SO₂ |
| H | Cl | H | O | SO₂ |
| H | Cl | CH₃ | O | SO₂ |
| H | H | H | S | S |
| H | CH₃ | H | S | S |
| H | CH₃ | CH₃ | S | S |
| H | CH₃ | Cl | S | S |
| H | Cl | H | S | S |
| H | Cl | CH₃ | S | S |
| H | H | H | SO₂ | SO₂ |
| H | CH₃ | H | SO₂ | SO₂ |
| H | CH₃ | CH₃ | SO₂ | SO₂ |
| H | CH₃ | Cl | SO₂ | SO₂ |
| H | Cl | H | SO₂ | SO₂ |
| H | Cl | CH₃ | SO₂ | SO₂ |
| S(O)₂(4-CH₃Ph) | CH₃ | CH₃ | O | S |
| S(O)₂(4-CH₃Ph) | CH₃ | CH₃ | O | SO₂ |
| S(O)₂(4-CH₃Ph) | CH₃ | CH₃ | S | S |
| S(O)₂(4-CH₃Ph) | CH₃ | CH₃ | SO₂ | SO₂ |
| C(=O)(4-CH₃Ph) | CH₃ | CH₃ | O | S |
| C(=O)(4-CH₃Ph) | CH₃ | CH₃ | O | SO₂ |
| C(=O)(4-CH₃Ph) | CH₃ | CH₃ | S | S |
| C(=O)(4-CH₃Ph) | CH₃ | CH₃ | SO₂ | SO₂ |
| C(=O)CH(CH₃)₂ | CH₃ | CH₃ | O | S |
| C(=O)CH(CH₃)₂ | CH₃ | CH₃ | O | SO₂ |
| C(=O)CH(CH₃)₂ | CH₃ | CH₃ | S | S |
| C(=O)CH(CH₃)₂ | CH₃ | CH₃ | SO₂ | SO₂ |
| C(=O)OCH(CH₃)₂ | CH₃ | CH₃ | O | S |
| C(=O)OCH(CH₃)₂ | CH₃ | CH₃ | O | SO₂ |
| C(=O)OCH(CH₃)₂ | CH₃ | CH₃ | S | S |
| C(=O)OCH(CH₃)₂ | CH₃ | CH₃ | SO₂ | SO₂ |
| C(=O)OCH₃ | CH₃ | CH₃ | O | S |
| C(=O)OCH₃ | CH₃ | CH₃ | O | SO₂ |
| C(=O)OCH₃ | CH₃ | CH₃ | S | S |
| C(=O)OCH₃ | CH₃ | CH₃ | SO₂ | SO₂ |

TABLE 5

[Structure: isoxazole with cyclopropyl, C(=O) linked to 2,6-dimethylphenyl fused ring with A, B, X]

| X | A | B |
|---|---|---|
| CH₂ | O | S |
| SO₂ | O | S |
| CH₂ | O | SO₂ |
| SO₂ | O | SO₂ |
| CH₂ | S | S |
| SO₂ | S | S |
| CH₂ | SO₂ | SO₂ |
| SO₂ | SO₂ | SO₂ |

TABLE 6

[Structure: isoxazole with cyclopropyl, C(=O) linked to 2,6-dimethylphenyl fused ring with A, B, X]

| X | A | B |
|---|---|---|
| CH | O | S |
| N | O | S |
| CH | O | SO₂ |
| N | O | SO₂ |
| CH | S | S |
| N | S | S |
| CH | SO₂ | SO₂ |
| N | SO₂ | SO₂ |

TABLE 7

[Structure: cyclopropyl-C(=O)-CH(CN)-C(=O)-linked to 2,6-dimethylphenyl fused ring with A, B, X]

| X | A | B |
|---|---|---|
| CH₂ | O | S |
| SO₂ | O | S |
| CH₂ | O | SO₂ |
| SO₂ | O | SO₂ |
| CH₂ | S | S |
| SO₂ | S | S |
| CH₂ | SO₂ | SO₂ |
| SO₂ | SO₂ | SO₂ |

TABLE 8

[Structure: cyclopropyl-C(=O)-CH(CN)-C(=O)-phenyl ring with CH3 groups at 2,6 positions, substituted at position with a fused ring containing A, B, and X positions]

| X | A | B |
|---|---|---|
| CH | O | S |
| N | O | S |
| CH | O | SO₂ |
| N | O | SO₂ |
| CH | S | S |
| N | S | S |
| CH | SO₂ | SO₂ |
| N | SO₂ | SO₂ |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. N o. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

Example A

High Strength Concentrate

| Compound 2 | 98.5% |
|---|---|
| silica aerogel | 0.5% |

-continued

| synthetic amorphous fine silica | 1.0%. |

Example B

Wettable Powder

| Compound 3 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| Compound 4 | 10.0% |
| attapulgite granules (low volatile matter, 0.71/0.30 mm; U.S.S. No. 20–50 sieves) | 90.0%. |

Example D

Extruded Pellet

| Compound 5 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azafenidin, azimsulfuron, benazolin, benazolin-ethyl, benfluralin, benfuresate, bensulfuron-methyl, bensulide, bentazone, bifenox, bispyribac and its sodium salt, bromacil, bromoxynil, bromoxynil octanoate, butachlor, butralin, butroxydim (ICIA0500), butylate, caloxydim (BAS 620H), carfentrazone-ethyl, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methylethyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethoxysulfuron, fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupyrsulfuron-methyl and its sodium salt, fluridone, flurochloridone, fluroxypyr, fluthiacet-methyl, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl)amino]carbonyl]amino]sulfonyl]-1-(2-pyridinyl)-1H-pyrazole4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, oxasulfuron, oxyfluorfen, paraquat dichloride, pebulate, pendimethalin, pentoxazone (KPP-314), perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyriminobac-methyl, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA005 1), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, triaziflam, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

The following Tests demonstrate the control efficacy of the compounds of this invention against specific weeds. The weed control afforded by the compounds is not limited, however, to these species. See Index Tables A and B for compound descriptions. The abbreviation "dec" indicates that the compound appeared to decompose on melting. The abbreviation "Ex." stands for "Example" and is followed by a number indicating in which example the compound is prepared.

INDEX TABLE A

| Cmpd | Structure | mp (°C.) |
|---|---|---|
| 1 (Ex. 1) | 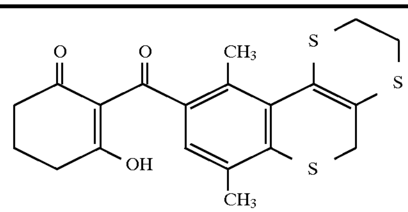 | 95 (dec)* |
| 2 (Ex. 2) | 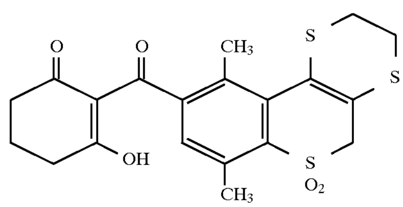 | 208–213* |
| 3 (Ex. 3) | 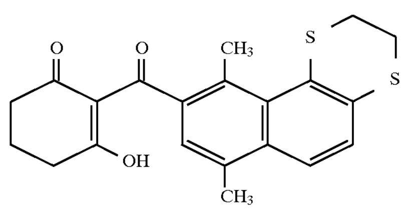 | * |
| 4 (Ex. 4) | 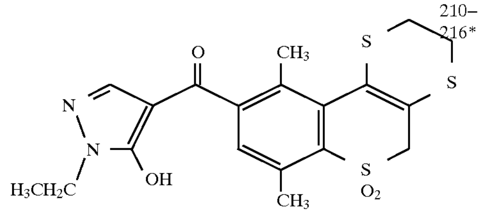 | 210–216* |
| 5 | 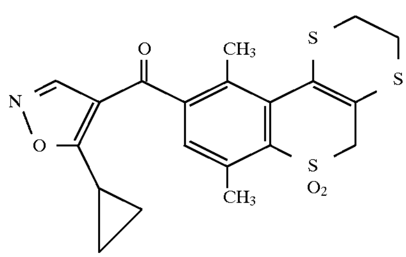 | 202–203 |
| 6 | | * |
| 7 | | * |
| 8 | | 189–192 |

*See Index Table B for $^1$H NMR data.

INDEX TABLE B

| Cmpd No. | $^1$H NMR Data (CDCl$_3$ solution unless indicated otherwise)[a] |
|---|---|
| 1 | δ 2.06 (m, 2H), 2.30 (s, 3H), 2.34 (s, 3H), 2.30–2.90 (m, 4H), 3.05 (m, 2H), 3.22 (br s, 2H), 3.39 (m, 2H), 6.70 (s, 1H) |
| 2 | δ 2.05 (m, 2H), 2.28 (s, 3H), 2.45 (m, 2H), 2.64 (s, 3H), 2.79 (m, 2H), 3.11 (m, 2H), 3.50 (m, 2H), 3.85 (s, 2H), 6.82 (s, 1H) |
| 3 | δ 2.05 (m, 2H), 2.44 (m, 2H), 2.59 (s, 3H), 2.84 (s, 3H), 2.75–3.00 (m, 4H), 3.47 (t, 2H), 6.93 (s, 1H), 7.44 (d, 1H), 7.68 (d, 1H) |
| 4 | δ 1.46 (t, 3H), 2.44 (s, 3H), 2.70 (s, 3H), 3.11 (m, 2H), 3.53 (m, 2H), 3.86 (s, 2H), 4.07 (m, 2H), 7.20 (s, 1H), 7.35 (s, 1H) |
| 6 | δ 1.12 (m, 2H), 1.15 (s, 9H), 1.20 (m, 2H), 2.42 (s, 3H), 2.65 (s, 3H), 3.18 (m, 2H), 3.47 (m, 2H), 3.79 (s, 2H), 7.00 (s, 1H) |
| 7 | δ 2.39 (s, 3H), 2.50 (s, 3H), 2.65 (s, 3H), 3.14 (m, 2H), 3.46 (m, 2H), 3.47 (s, 3H), 3.84 (s, 2H), 6.98 (s, 1H) |

[a] $^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION

Test A

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which included a surfactant.

At the same time, these crop and weed species were also treated with postemergence applications of test chemicals formulated in the same manner. Plants ranged in height from 2 to 18 cm (1- to 4-leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (—) response test result.

TABLE A

| | POSTEMERGENCE | | | | | | | | | |
|---|---|---|---|---|---|---|---|---|---|---|
| | Rate 400 g/ha | | Rate 200 g/ha | | | Rate 100 g/ha | | Rate 50 g/ha | | |
| | 1 | 3 | 2 | 4 | 8 | 1 | 3 | 2 | 4 | 8 |
| Barley | 1 | 6 | 7 | 1 | 3 | 0 | 5 | 4 | 0 | 1 |
| Barnyardgrass | 9 | 9 | 9 | 9 | 9 | 8 | 9 | 9 | 9 | 9 |
| Bedstraw | 6 | 8 | 8 | 9 | 6 | 5 | 7 | 8 | 7 | 5 |
| Blackgrass | 0 | 2 | 3 | 0 | 5 | 0 | 2 | 1 | 0 | 2 |
| Chickweed | 8 | 9 | 9 | 9 | 8 | 6 | 9 | 8 | 7 | 6 |
| Cocklebur | 6 | 7 | 9 | 9 | 6 | 4 | 7 | 9 | 9 | 6 |
| Corn | 2 | 3 | 1 | 1 | 4 | 1 | 2 | 0 | 0 | 3 |
| Cotton | 4 | 10 | 9 | 9 | 10 | 4 | 9 | 9 | 3 | 9 |
| Crabgrass | 9 | 9 | 9 | 8 | 9 | 6 | 9 | 4 | 2 | 8 |
| Downy brome | 0 | 2 | 7 | 0 | 2 | 0 | 1 | 4 | 0 | 1 |
| Giant foxtail | 4 | 9 | 9 | 8 | 8 | 2 | 7 | 3 | 4 | 6 |
| Lambsquarters | 9 | 9 | 10 | 9 | 9 | 9 | 9 | 9 | 9 | 9 |
| Morningglory | 9 | 9 | 8 | 6 | 8 | 6 | 8 | 9 | 2 | 4 |
| Nutsedge | 0 | 6 | — | 1 | 0 | 0 | 4 | 0 | — | 0 |
| Rape | 8 | 9 | 9 | 7 | 10 | 7 | 8 | 6 | 6 | 8 |
| Rice | 4 | 9 | 5 | 2 | 9 | 2 | 9 | 2 | 1 | 9 |
| Sorghum | 7 | 10 | 9 | 8 | 9 | 3 | 8 | 9 | 3 | 7 |
| Soybean | 8 | 8 | 9 | 5 | 9 | 4 | 7 | 8 | 4 | 2 |
| Sugar beet | 10 | 10 | 10 | 10 | 10 | 9 | 9 | 10 | 10 | 10 |
| Velvetleaf | 9 | 10 | 10 | 9 | 10 | 9 | 10 | 10 | 9 | 10 |
| Wheat | 2 | 5 | 7 | 1 | 4 | 0 | 3 | 5 | 0 | 2 |
| Wild buckwheat | 3 | 6 | 8 | 7 | 6 | 0 | 6 | 8 | 5 | 4 |
| Wild oat | 2 | 7 | 6 | 2 | 9 | 1 | 5 | 3 | 0 | 4 |

| | PREEMERGENCE | | | | | | | | | |
|---|---|---|---|---|---|---|---|---|---|---|
| | COMPOUND | | | | | | | | | |
| | Rate 400 g/ha | | Rate 200 g/ha | | | Rate 100 g/ha | | Rate 50 g/ha | | |
| | 1 | 3 | 2 | 4 | 8 | 1 | 3 | 2 | 4 | 8 |
| Barley | 0 | 0 | 0 | 0 | 0 | 0 | 0 | 0 | 0 | 0 |
| Barnyardgrass | 0 | 1 | 7 | 0 | 0 | 0 | 0 | 0 | 0 | 0 |
| Bedstraw | 0 | 0 | 1 | 2 | 0 | 0 | 0 | 0 | 0 | 0 |
| Blackgrass | 0 | 0 | 0 | 0 | 0 | 0 | 0 | 0 | 0 | 0 |
| Chickweed | 0 | 0 | 4 | 6 | 1 | 0 | 0 | 0 | 3 | 0 |
| Cocklebur | 0 | 0 | 0 | 0 | 0 | 0 | 0 | 0 | 0 | 0 |
| Corn | 0 | 0 | 0 | 0 | 0 | 0 | 0 | 0 | 0 | 0 |
| Cotton | 0 | 2 | 0 | 0 | 0 | 0 | 0 | 0 | 0 | 0 |
| Crabgrass | 1 | 4 | 6 | 3 | 8 | 0 | 1 | 0 | 0 | 1 |
| Downy brome | 0 | 0 | 0 | 0 | 0 | 0 | 0 | 0 | 0 | 0 |
| Giant foxtail | 0 | 0 | 1 | 0 | 1 | 0 | 0 | 0 | 0 | 0 |
| Lambsquarters | 9 | 9 | 10 | 10 | 9 | 0 | 9 | 9 | 6 | 4 |
| Morningglory | 0 | 0 | 2 | 0 | 0 | 0 | 0 | 2 | 0 | 0 |
| Nutsedge | — | 0 | 0 | 0 | 0 | 0 | 0 | 0 | 0 | 0 |
| Rape | 0 | 3 | 0 | 5 | 4 | 0 | 0 | 0 | 0 | 2 |
| Rice | 0 | 0 | 1 | 0 | 0 | 0 | 0 | 0 | 0 | 0 |
| Sorghum | 0 | 1 | 0 | 0 | 0 | 0 | 0 | 0 | 0 | 0 |
| Soybean | 0 | 0 | 6 | 0 | 0 | 0 | 0 | 0 | 0 | 0 |
| Sugar beet | 4 | 0 | 9 | 7 | 5 | 0 | 0 | 0 | 0 | 4 |
| Velvetleaf | — | 9 | 10 | 8 | 4 | — | — | 3 | 1 | 0 |
| Wheat | 0 | 0 | 0 | 0 | 0 | 0 | 0 | 0 | 0 | 0 |

TABLE A-continued

| | | | | | | | | | | |
|---|---|---|---|---|---|---|---|---|---|---|
| Wild buckwheat | 0 | 0 | 0 | 0 | 0 | 0 | 0 | 0 | 0 | 0 |
| Wild oat | 0 | 0 | 0 | 0 | 0 | 0 | 0 | 0 | 0 | 0 |

Test B

The compounds evaluated in this test were formulated in a non-phytotoxic solvent mixture which included a surfactant and applied to the soil surface before plant seedlings emerged (preemergence application), to water that covered the soil surface (flood application), and to plants that were in the one- to four-leaf stage (postemergence application). A sandy loam soil was used for the preemergence and postemergence tests, while a silt loam soil was used in the flood application. Water depth was approximately 2.5 cm for the flood application and was maintained at this level for the duration of the test.

Plant species in the preemergence and postemergence tests consisted of barnyardgrass (*Echinochloa crus-galli*), winter barley (*Hordeum vulgare*), bedstraw (*Galium aparine*), blackgrass (*Alopecurus myosuroides*), chickweed (*Stellaria media*), cocklebur (*Xanthium strumarium*), corn 1 (*Zea mays*), cotton (*Gossypium hirsutum*), crabgrass (*Digitaria sanguinalis*), downy brome (*Bromus tectorum*), giant foxtail (*Setaria faberi*), johnsongrass (*Sorghum halpense*), lambsquarters (*Chenopodium album*), morningglory (*Ipomoea hederacea*), pigweed (*Amaranthus retroflexus*), rape (*Brassica napus*), Italian ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Additionally two corn varieties were treated with postemergence applications. These inbred lines were designated Corn 2 and Corn 3. Plant species in the flood test consisted of rice (*Oryza sativa*), umbrella sedge (*Cyperus difformis*), duck salad (*Heteranthera limosa*) and barnyardgrass 1 (*Echinochloa crus-galli*).

All plant species were grown using normal greenhouse practices. Visual evaluations of injury expressed on treated plants, when compared to untreated controls, were recorded approximately fourteen to twenty one days after application of the test compound. Plant response to the test compound is summarized in Table B, recorded on a 0 to 100 scale where 0 is no effect and 100 is complete control. A dash (-) response means no test result.

TABLE B

| COMPOUND | | | COMPOUND | | COMPOUND | | |
|---|---|---|---|---|---|---|---|
| Rate 250 g/ha POSTEMERGENCE | 2 | 4 | Rate 250 g/ha PREEMERGENCE | 2 | Rate 125 g/ha POSTEMERGENCE | 2 | 4 |
| Barley (winter) | 45 | — | Barley (winter) | 0 | Barley (winter) | 20 | — |
| Barnyardgrass | 95 | — | Barnyardgrass | 0 | Barnyardgrass | 90 | — |
| Barnyardgrass 1 | 70 | 15 | Bedstraw | 20 | Barnyardgrass 1 | 30 | 0 |
| Bedstraw | 75 | — | Blackgrass | 0 | Bedstraw | 70 | — |
| Blackgrass | 50 | — | Chickweed | 80 | Blackgrass | 30 | — |
| Chickweed | 100 | — | Cocklebur | 0 | Chickweed | 95 | — |
| Cocklebur | 90 | — | Corn 1 | 0 | Cocklebur | 90 | — |
| Corn 1 | 0 | — | Cotton | 0 | Corn 1 | 0 | — |
| Corn 2 | 15 | — | Crabgrass | 100 | Corn 2 | 0 | — |
| Corn 3 | 75 | — | Downy brome | 0 | Corn 3 | 50 | — |
| Cotton | 90 | — | Giant foxtail | 0 | Cotton | 90 | — |
| Crabgrass | 95 | — | Italn. ryegrass | 0 | Crabgrass | 95 | — |
| Downy brome | 60 | — | Johnsongrass | 35 | Downy brome | 40 | — |
| Ducksalad | 90 | 80 | Lambsquarter | 100 | Ducksalad | 80 | 70 |
| Giant foxtail | 90 | — | Morningglory | 0 | Giant foxtail | 70 | — |
| Italn. ryegrass | 40 | — | Rape | 0 | Italn. ryegrass | 20 | — |
| Johnsongrass | 70 | — | Redroot pigweed | 0 | Johnsongrass | 70 | — |
| Lambsquarter | 100 | — | Soybean | 0 | Lambsquarter | 100 | — |
| Morningglory | 95 | — | Speedwell | 100 | Morningglory | 90 | — |
| Rape | 100 | — | Sugar beet | 100 | Rape | 95 | — |
| Redroot pigweed | 70 | — | Velvetleaf | 100 | Redroot pigweed | 60 | — |
| Rice japonica | 0 | 0 | Wheat | 0 | Rice japonica | 0 | 0 |
| Soybean | 90 | — | Wild buckwheat | 0 | Soybean | 90 | — |
| Speedwell | 100 | — | Wild oat | 0 | Speedwell | 100 | — |
| Sugar beet | 100 | — | | | Sugar beet | 100 | — |
| Umbrella sedge | 70 | 55 | | | Umbrella sedge | 50 | 50 |
| Velvetleaf | 100 | — | | | Velvetleaf | 100 | — |
| Wheat | 80 | — | | | Wheat | 50 | — |
| Wild buckwheat | 50 | — | | | Wild buckwheat | 50 | — |
| Wild oat | 80 | — | | | Wild oat | 50 | — |

| COMPOUND | | COMPOUND | | | |
|---|---|---|---|---|---|
| Rate 125 g/ha PREEMERGENCE | 2 | Rate 62 g/ha POSTEMERGENCE | 2 | 3 | 4 |
| Barley (winter) | 0 | Barley (winter) | 10 | 0 | — |
| Barnyardgrass | 0 | Barnyardgrass | 90 | 90 | — |

TABLE B-continued

| | | | | | |
|---|---|---|---|---|---|
| Bedstraw | 0 | Barnyardgrass 1 | 20 | 0 | 0 |
| Blackgrass | 0 | Bedstraw | 70 | 50 | — |
| Chickweed | 30 | Blackgrass | 20 | 0 | — |
| Cocklebur | 0 | Chickweed | 90 | 90 | — |
| Corn 1 | 0 | Cocklebur | 80 | 70 | — |
| Cotton | 0 | Corn 1 | 0 | 0 | — |
| Crabgrass | 80 | Corn 2 | 0 | — | — |
| Downy brome | 0 | Corn 3 | 30 | — | — |
| Giant foxtail | 0 | Cotton | 70 | 20 | — |
| Italn. ryegrass | 0 | Crabgrass | 95 | 90 | — |
| Johnsongrass | 0 | Downy brome | 30 | 0 | — |
| Lambsquarter | 100 | Ducksalad | 40 | 0 | 40 |
| Morningglory | 0 | Giant foxtail | 60 | 70 | — |
| Rape | 0 | Italn. ryegrass | 10 | 0 | — |
| Redroot pigweed | 0 | Johnsongrass | 60 | 70 | — |
| Soybean | 0 | Lambsquarter | 100 | 90 | — |
| Speedwell | 100 | Morningglory | 90 | 70 | — |
| Sugar beet | 100 | Rape | 70 | 80 | — |
| Velvetleaf | 100 | Redroot pigweed | 60 | 90 | — |
| Wheat | 0 | Rice japonica | 0 | 0 | 0 |
| Wild buckwheat | 0 | Soybean | 85 | 80 | — |
| Wild oat | 0 | Speedwell | 100 | 70 | — |
| | | Sugar beet | 100 | 70 | — |
| | | Umbrella sedge | 10 | 0 | 40 |
| | | Velvetleaf | 100 | 90 | — |
| | | Wheat | 30 | 0 | — |
| | | Wild buckwheat | 30 | 20 | — |
| | | Wild oat | 35 | 0 | — |

| | COMPOUND | | | COMPOUND | |
|---|---|---|---|---|---|
| Rate 62 g/ha PREEMERGENCE | 2 | 3 | Rate 31 g/ha POSTEMERGENCE | 2 | 3 | 4 |
| Barley (winter) | 0 | 0 | Barley (winter) | 0 | 0 | — |
| Barnyardgrass | 0 | 0 | Barnyardgrass | 90 | 90 | — |
| Bedstraw | 0 | 0 | Barnyardgrass 1 | 10 | 0 | 0 |
| Blackgrass | 0 | 0 | Bedstraw | 70 | 30 | — |
| Chickweed | 0 | 0 | Blackgrass | 20 | 0 | — |
| Cocklebur | 0 | 0 | Chickweed | 90 | 50 | — |
| Corn 1 | 0 | 0 | Cocklebur | 70 | 40 | — |
| Cotton | 0 | 0 | Corn 1 | 0 | 0 | — |
| Crabgrass | 70 | 0 | Corn 2 | 0 | 10 | — |
| Downy brome | 0 | 0 | Corn 3 | 30 | 40 | — |
| Giant foxtail | 0 | 0 | Cotton | 50 | 20 | — |
| Italn. ryegrass | 0 | 0 | Crabgrass | 90 | 90 | — |
| Johnsongrass | 0 | 30 | Downy brome | 20 | 0 | — |
| Lambsquarter | 100 | 60 | Ducksalad | 0 | 0 | 10 |
| Morningglory | 0 | 0 | Giant foxtail | 20 | 40 | — |
| Rape | 0 | 10 | Italn. ryegrass | 0 | 0 | — |
| Redroot pigweed | 0 | 0 | Johnsongrass | 30 | 70 | — |
| Soybean | 0 | 0 | Lambsquarter | 90 | 80 | — |
| Speedwell | 0 | — | Morningglory | 90 | 70 | — |
| Sugar beet | 70 | 10 | Rape | 60 | 60 | — |
| Velvetleaf | 100 | 20 | Redroot pigweed | 35 | 90 | — |
| Wheat | 0 | 0 | Rice japonica | 0 | 0 | 0 |
| Wild buckwheat | 0 | 0 | Soybean | 80 | 70 | — |
| Wild oat | 0 | 0 | Speedwell | 95 | 60 | — |
| | | | Sugar beet | 90 | 70 | — |
| | | | Umbrella sedge | 0 | 0 | 20 |
| | | | Velvetleaf | 90 | 90 | — |
| | | | Wheat | 10 | 0 | — |
| | | | Wild buckwheat | 30 | 20 | — |
| | | | Wild oat | 30 | 0 | — |

| | COMPOUND | | | COMPOUND | | COMPOUND |
|---|---|---|---|---|---|---|
| Rate 31 g/ha PREEMERGENCE | 2 | 3 | Rate 16 g/ha POSTEMERGENCE | | 3 | Rate 8 g/ha POSTEMERGENCE | 3 |
| Barley (winter) | 0 | 0 | Barley (winter) | | 0 | Barley (winter) | 0 |
| Barnyardgrass | 0 | 0 | Barnyardgrass | | 80 | Barnyardgrass | 80 |
| Bedstraw | 0 | 0 | Barnyardgrass 1 | | 0 | Barnyardgrass 1 | 0 |
| Blackgrass | 0 | 0 | Bedstraw | | 20 | Bedstraw | 10 |
| Chickweed | 0 | 0 | Blackgrass | | 0 | Blackgrass | 0 |
| Cocklebur | 0 | 0 | Chickweed | | 40 | Chickweed | 40 |
| Corn 1 | 0 | 0 | Cocklebur | | 40 | Cocklebur | 20 |
| Cotton | 0 | 0 | Corn 1 | | 0 | Corn 1 | 0 |
| Crabgrass | 50 | 0 | Corn 2 | | 0 | Corn 2 | 0 |
| Downy brome | 0 | 0 | Corn 3 | | 25 | Corn 3 | 15 |
| Giant foxtail | 0 | 0 | Cotton | | — | Cotton | 0 |

TABLE B-continued

| | | | | | | | |
|---|---|---|---|---|---|---|---|
| Italn. ryegrass | 0 | 0 | Crabgrass | 70 | Crabgrass | 60 |
| Johnsongrass | 0 | 0 | Downy brome | 0 | Downy brome | 0 |
| Lambsquarter | 80 | 30 | Ducksalad | 0 | Ducksalad | 0 |
| Morningglory | 0 | 0 | Giant foxtail | 20 | Giant foxtail | 10 |
| Rape | 0 | 0 | Italn. ryegrass | 0 | Italn. ryegrass | 0 |
| Redroot pigweed | 0 | 0 | Johnsongrass | 30 | Johnsongrass | 20 |
| Soybean | 0 | 0 | Lambsquarter | 70 | Lambsquarter | 40 |
| Speedwell | 0 | — | Morningglory | 70 | Morningglory | 40 |
| Sugar beet | 20 | 0 | Rape | 30 | Rape | 20 |
| Velvetleaf | 40 | 0 | Redroot pigweed | 90 | Redroot pigweed | 0 |
| Wheat | 0 | 0 | Rice japonica | 0 | Rice japonica | 0 |
| Wild buckwheat | 0 | 0 | Soybean | 60 | Soybean | 40 |
| Wild oat | 0 | 0 | Speedwell | 40 | Speedwell | 30 |
| | | | Sugar beet | 40 | Sugar beet | 20 |
| | | | Umbrella sedge | 0 | Umbrella sedge | 0 |
| | | | Velvetleaf | 90 | Velvetleaf | 70 |
| | | | Wheat | 0 | Wheat | 0 |
| | | | Wild buckwheat | — | Wild buckwheat | 0 |
| | | | Wild oat | 0 | Wild oat | 0 |

Test C

Plastic pots were partially filled with silt loam soil. The soil was then saturated with water. Rice (*Oryza saliva*) seed or seedlings at the 2.0-leaf stage, weed seeds, tubers or plant parts selected from arrowhead (*Sagittaria rigida*), common water plantain (*Alisma plantago-aquatica*), ducksalad (*Heteranthera limosa*), gooseweed (*Sphenoclea zeylanica*), monochoria (*Monochoria vaginalis*), river bullrush (*Scirpus fluviatikis*), redstem (Ammania species), rice flatsedge (*Cyperus iria*), smallflower flatsedge (*Cyperus difformis*), tighthead sprangletop (*Leptochloa fasicularis*) and water-clover (*Marsilea quadrifolia*) were planted into this soil. The various rice seed types and methods are designated as: Rice indica 1 (2 leaf direct seeded indica type rice), Rice indica 3 (2 leaf transplanted indica type rice), Rice japonica 1 (2 leaf direct seeded japonica type rice) and Rice japonica 2 (2 leaf transplanted japonica type rice). Plantings and waterings of these crops and weed species were adjusted to produce plants of appropriate size for the test. At the 2-leaf stage, water levels were raised to 3 cm above the soil surface and maintained at this level throughout the test. Chemical treatments were formulated in a non-phytotoxic solvent mixture which included a surfactant and applied directly to the paddy water by pipette, or to the plant foliage by an air pressure-assisted, calibrated belt-conveyer spray system.

Treated plants and controls were maintained in a greenhouse for approximately 21 days, after which all species were compared to controls and visually evaluated. Plant response ratings, summarized in Table C, are reported on a 0 to 100 scale where 0 is no effect and 100 is complete control. A dash (—) response means no test result.

TABLE C

| | COMPOUMD | | | | | | | | | | | | | | | |
|---|---|---|---|---|---|---|---|---|---|---|---|---|---|---|---|---|
| | Rate 750 g/ha | Rate 500 g/ha | Rate 375 g/ha | Rate 250 g/ha | | Rate 175 g/ha | Rate 125 g/ha | | Rate 75 g/ha | | Rate 64 g/ha | |
| | 4 | 4 | 2 | 2 | 4 | 2 | 2 | 4 | 2 | 2 | 4 |
| Paddy/silt lo | | | | | | | | | | | | |
| Arrowhead | — | — | 70 | 50 | — | 40 | 30 | — | 10 | — | — |
| C. waterplantai | — | — | 95 | 95 | — | 80 | 70 | — | 65 | — | — |
| Ducksalad | 100 | 98 | 90 | 90 | 98 | 85 | 70 | 98 | — | 0 | 20 |
| Gooseweed | — | — | 100 | 00 | — | 100 | 100 | — | 98 | — | — |
| Monochoria | — | — | 95 | 95 | — | 90 | 85 | — | 60 | — | — |
| R. bulrush | — | — | 95 | 95 | — | 85 | 80 | — | 40 | — | — |
| Redstem | 90 | 85 | 90 | 95 | 20 | 90 | 75 | 0 | — | 0 | 0 |
| Rice flatsedge | 80 | 70 | 95 | 95 | 30 | 95 | 80 | 35 | — | 60 | 0 |
| Rice indica 1 | 15 | 15 | 10 | 10 | 15 | 10 | 0 | 15 | — | 0 | 15 |
| Rice indica 3 | 20 | 20 | 0 | 15 | 15 | 10 | 10 | 10 | — | 10 | 20 |
| Rice japonica 1 | — | — | 0 | 10 | — | 10 | 10 | — | 0 | — | — |
| Rice japonica 2 | — | — | 10 | 15 | — | 15 | 10 | — | 10 | — | — |
| S. flatsedge | 100 | 98 | 95 | 90 | 85 | 85 | 75 | 80 | — | 30 | 30 |
| T. sprangletop | 40 | 15 | 95 | 95 | 20 | 95 | 85 | 0 | — | 0 | 10 |
| Water-clover | — | — | 80 | 25 | — | 25 | 10 | — | 0 | — | — |

Test D

Compounds evaluated in this test were formulated in a non-phytotoxic solvent mixture and applied to the surface of the water which was contained in each pot. Individual containers of barnyardgrass (*Echinochloa oryzicola*), smallflower umbrella sedge (*Cyperus difformis*), common falsepimpernel (*Lindernia procumbens*), monochoria (*Monochoria vaginalis*) and scirpus (*Scirpus juncoides*) were seeded and allowed to grow until the desired leaf stage of development was reached. A Saita clay loam soil was used for this propagation. Japonica rice (*Oryza sativa*) was transplanted at 0 and 2 cm depth (designated Rice japonica 1 and Rice japonica 2, respectively) five days before application of the test compound to the water surface. An early and late stage of each weed species was treated, the stage of development being related to the concurrent planting of *Scirpus juncoides* which was then treated at the 1.5 (early (1)) and the 2.5 (late (2)) leaf stage.

Treated plants and untreated controls were maintained under greenhouse conditions for twenty to thirty days at greenhouse for approximately eleven days, after which all treated plants were compared to untreated controls and visually evaluated for injury. Plant response ratings, summarized in Table E, are based on a 0 to 10 scale where 0 is no effect and 10 is complete control. A dash (—) response means no test results.

TABLE E

| | COMPOUND | | COMPOUND |
|---|---|---|---|
| Rate 2000 g/ha PREEMERGENCE | 6 | Rate 1000 g/ha POSTEMERGENCE | 6 |
| Barnyardgrass | 8 | Barnyardgrass | 7 |
| Crabgrass | 9 | Crabgrass | 7 |
| Morningglory | 2 | Morningglory | 8 |
| Velvetleaf | 9 | Velvetleaf | 9 | which time treated plants were compared to untreated controls and visually evaluated. Plant response ratings, summarized in Table D, are based upon a 0 to 100 scale where 0 is no effect and 100 is complete control. A dash response (—) indicated that no test result was recorded.

TABLE D

| COMPOUND | | COMPOUND | |
|---|---|---|---|
| Rate 125 g/ha Flood Saita soi | 1 | Rate 64 g/ha Flood Saita soi | 1 |
| Barnyardgrass 1 | 30 | Barnyardgrass 1 | 0 |
| Barnyardgrass 2 | 0 | Barnyardgrass 2 | 0 |
| Falsepimperne11 | 100 | Falsepimperne11 | 100 |
| Falsepimperne12 | 85 | Falsepimperne12 | 85 |
| Monochoria 1 | 50 | Monochoria 1 | 30 |
| Monochoria 2 | 40 | Monochoria 2 | 30 |
| Rice japonica 1 | 10 | Rice japonica 1 | 0 |
| Rice japonica 2 | 0 | Rice japonica 2 | 0 |
| S. flatsedge 1 | 50 | S. flatsedge 1 | 50 |
| S. flatsedge 2 | 40 | S. flatsedge 2 | 30 |
| Scirpus 1 | 45 | Scirpus 1 | 40 |
| Scirpus 2 | 40 | Scirpus 2 | 30 |
| COMPOUND | | COMPOUND | |
| Rate 32 g/ha Flood Saita soi | 1 | Rate 16 g/ha Flood Saita soi | 1 |
| Barnyardgrass 1 | 0 | Barnyardgrass 1 | 0 |
| Barnyardgrass 2 | 0 | Barnyardgrass 2 | 0 |
| Falsepimperne11 | 95 | Falsepimperne11 | 90 |
| Falsepimperne12 | 85 | Falsepimperne12 | 80 |
| Monochoria 1 | 20 | Monochoria 1 | 0 |
| Monochoria 2 | 0 | Monochoria 2 | 0 |
| Rice japonica 1 | 10 | Rice japonica 1 | 0 |
| Rice japonica 2 | 0 | Rice japonica 2 | 0 |
| S. flatsedge 1 | 20 | S. flatsedge 1 | 0 |
| S. flatsedge 2 | 20 | S. flatsedge 2 | 20 |
| Scirpus 1 | 30 | Scirpus 1 | 0 |
| Scirpus 2 | 10 | Scirpus 2 | 0 |

Test E

Seeds of barnyardgrass (*Echinochloa crus-galli*), crabgrass (Digitaria spp.), morningglory (Ipomoea spp.), and velvetleaf (*Abutilon theophrasti*) were planted into a sandy loam soil and treated preemergence by soil drench with test chemicals formulated in a non-phytotoxic solvent mixture which included a surfactant. At the same time, these crop and weed species were also treated postemergence sprayed to runoff, with test chemicals formulated in the same manner.

Plants ranged in height from two to eighteen cm and were in the one to two leaf stage for the postemergence treatment. Treated plants and untreated controls were maintained in a

What is claimed is:

1. A compound selected from Formula I,N-oxides and agriculturally suitable salts thereof,

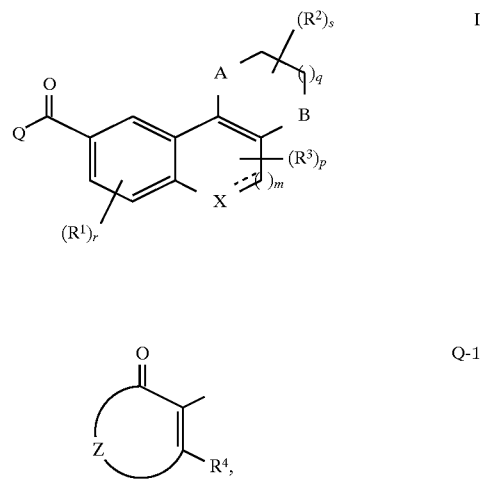

wherein

Q is $$\text{Q-1}$$

Z is selected from the group —CH$_2$CH$_2$CH$_2$—, —OCH$_2$CH$_2$—, —O—CH=CH—, —OCH$_2$O—, —CH$_2$OCH$_2$—, —CH$_2$S(O)$_n$CH$_2$—, —CH$_2$C(O)CH$_2$—, —CH$_2$CH$_2$—, —OCH$_2$— and —SCH$_2$—, each group optionally substituted with one to four R$^5$, and the directionality of the Z linkage is defined such that the moiety depicted on the left side of the linkage is bonded to the carbonyl carbon of Q-1;

X is S(O)$_n$ or CH;

A is O or S(O)$_n$;

B is S(O)$_n$;

each R$^1$ is independently C$_1$–C$_6$ alkyl, C$_1$–C$_6$ haloalkyl, C$_1$–C$_6$ alkoxy, C$_1$–C$_6$ haloalkoxy, S(O)$_n$R$^{17}$, SO$_2$N(R$^{13}$)$_2$, halogen, cyano or nitro;

each R$^2$ is independently C$_1$–C$_3$alkyl;

each R$^3$ is independently C$_1$–C$_2$ alkyl;

R$^4$ is OR$^{14}$, SH, S(O)$_n$R$^{17}$, halogen or NR$^{15}$R$^{16}$; or R$^4$ is phenylthio or phenylsulfonyl, each optionally substituted with C$_1$–C$_3$ alkyl, halogen, cyano or nitro;

each R$^5$ is independently H, C$_1$–C$_3$ alkyl, C$_3$–C$_6$ alkenyl, C$_3$–C$_6$ alkynyl, C$_1$–C$_3$ alkoxy, formyl, C$_2$–C$_6$ alkoxycarbonyl, —CH$_2$(C$_1$–C$_3$ alkoxy), —CH(C$_1$–C$_3$ alkoxy)$_2$, C$_1$–C$_3$ alkylthio, cyano or halogen; or when two R$^5$ are attached to the same carbon atom, then said R$^5$ pair can be taken together to form —OCH$_2$CH$_2$O—, —OCH$_2$CH$_2$CH$_2$O—, —SCH$_2$CH$_2$S— or —SCH$_2$CH$_2$CH$_2$S—, each group optionally substituted with 1–4 CH$_3$;

each R$^{13}$ is independently H or C$_1$–C$_6$ alkyl;

R$^{14}$ is H, C$_1$–C$_6$ alkyl, C$_1$–C$_6$ haloyalkyl, C$_2$–C$_6$ alkoxyalkyl, formyl, C$_2$–C$_6$ alkylcarbonyl, C$_2$–C$_6$ alkoxycarbonyl, C(O)NR$^{15}$R$^{16}$ or SO$_2$R$^{17}$; or R$^{14}$ is phenyl, benzyl, benzoyl, —CH$_2$C(O)phenyl or phenylsulfonyl, each optionally substituted on the phenyl ring with C$_1$–C$_3$ alkyl, halogen, cyano or nitro;

R$^{15}$ is H or C$_1$–C$_6$ alkyl;

R$^{16}$ is C$_1$–C$_6$ alkyl or C$_1$–C$_6$ alkoxy; or

R$^{15}$ and R$^{16}$ can be taken together as CH$_2$CH$_2$, CH$_2$CH$_2$CH$_2$, CH$_2$CH$_2$CH$_2$CH$_2$, —CH$_2$CH$_2$CH$_2$CH$_2$CH$_2$— or —CH$_2$CH$_2$OCH$_2$CH$_2$—;

R$^{17}$ is C$_1$–C$_6$ alkyl or C$_1$–C$_6$ haloalkyl;

m is 0, 1 or 2;

each n is independently 0, 1 or 2;

p is 0, 1 or 2;

q is 1 or 2;

r is 0, 1, 2 or 3;

s is 0, 1, 2, 3 or 4;

provided that when m is 0 then X is other than N or CH; and wherein the dashed line in Formula I signifies either a single or double bond.

2. A compound of claim 1 wherein

A and B are independently S(O)$_n$; and

R$^1$ is C$_1$–C$_3$ alkyl, halogen, cyano or nitro.

3. A compound of claim 2 wherein

Z is —CH$_2$CH$_2$CH$_2$; and

R$^4$ is OR$^{14}$.

4. The compound of claim 3 which is selected from the group:

2-[(2,3-dihydro-7,10-dimethyl-6,6-dioxido-5H-1,4-dithiino[2,3-c][1]benzothiopyran-9-yl)carbonyl]-3-hydroxy-2-cyclohexen-1-one; and 2-[(2,3-dihydro-7,10-dimethylnaphtho[1,2-b]-1,4-dithiin-9-yl)carbonyl]-3-hydroxy-2-cyclohexen-1-one.

5. A herbicidal composition comprising a herbicidally effective amount of a compound of claim 1 and at least one of a surfactant, a solid diluent or a liquid diluent.

6. A method for controlling the growth of undesired vegetation comprising contacting the vegetation or its environment with a herbicidally effective amount of a compound of claim 1.

* * * * *